(12) United States Patent
Holop et al.

(10) Patent No.: US 12,285,226 B2
(45) Date of Patent: Apr. 29, 2025

(54) FLUX DISAMBIGUATION FOR TELEOPERATED SURGICAL SYSTEMS

(71) Applicant: INTUITIVE SURGICAL OPERATIONS, INC., Sunnyvale, CA (US)

(72) Inventors: Robert E. Holop, Santa Clara, CA (US); Thomas G. Cooper, Menlo Park, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1186 days.

(21) Appl. No.: 17/106,926

(22) Filed: Nov. 30, 2020

(65) Prior Publication Data

US 2021/0077207 A1 Mar. 18, 2021

Related U.S. Application Data

(62) Division of application No. 14/070,184, filed on Nov. 1, 2013, now Pat. No. 10,864,048.

(60) Provisional application No. 61/721,909, filed on Nov. 2, 2012.

(51) Int. Cl.
    *A61B 34/30* (2016.01)
    *A61B 18/14* (2006.01)
    *A61B 17/00* (2006.01)
    *A61B 18/00* (2006.01)

(52) U.S. Cl.
    CPC .............. *A61B 34/30* (2016.02); *A61B 18/14* (2013.01); *A61B 2017/00482* (2013.01); *A61B 2018/00178* (2013.01); *Y10S 901/41* (2013.01)

(58) Field of Classification Search
    CPC .................... A61B 34/30; A61B 18/14; A61B 2017/00482; A61B 2018/00178; Y10S 901/41
    See application file for complete search history.

(56) References Cited

U.S. PATENT DOCUMENTS

| 2,175,768 A | 10/1939 | Anthony |
| 2,249,618 A | 7/1941 | Perkins |
| 3,184,703 A | 5/1965 | Piscitello et al. |

(Continued)

FOREIGN PATENT DOCUMENTS

| CN | 101297760 A | 11/2008 |
| CN | 101902979 A | 12/2010 |

(Continued)

OTHER PUBLICATIONS

Extended European Search Report for Application No. EP20172390.5mailed on Jul. 15, 2020, 09 pages.

(Continued)

*Primary Examiner* — Michael F Peffley
*Assistant Examiner* — Bo Ouyang
(74) *Attorney, Agent, or Firm* — JONES ROBB, PLLC

(57) ABSTRACT

A method includes receiving at a controller of a teleoperated surgical system a first signal indicating that a surgical instrument is in an installed position at a patient side cart of the teleoperated surgical system, receiving at the controller a second signal indicating that the surgical instrument is in a flux connection state, and outputting a signal via the controller to provide feedback indicating that the surgical instrument is in the flux connection state.

11 Claims, 14 Drawing Sheets

(56) References Cited

U.S. PATENT DOCUMENTS

| | | | |
|---|---|---|---|
| 4,211,461 A | 7/1980 | Wescott | |
| 4,284,312 A | 8/1981 | Patchett et al. | |
| 5,180,316 A | 1/1993 | Miller et al. | |
| 5,350,314 A | 9/1994 | Saba | |
| 5,817,092 A | 10/1998 | Behl | |
| 6,036,637 A | 3/2000 | Kudo | |
| 6,040,537 A | 3/2000 | McClintock | |
| 6,074,388 A | 6/2000 | Tockweiler et al. | |
| 6,113,596 A | 9/2000 | Hooven et al. | |
| 6,262,754 B1 | 7/2001 | Watanabe et al. | |
| 6,338,657 B1 | 1/2002 | Harper et al. | |
| 6,450,978 B1 | 9/2002 | Brosseau et al. | |
| 6,463,822 B1 | 10/2002 | Bader et al. | |
| 6,493,608 B1 | 12/2002 | Niemeyer | |
| 6,522,906 B1 | 2/2003 | Salisbury, Jr. et al. | |
| 6,636,254 B1 | 10/2003 | Onishi et al. | |
| 6,702,617 B1 | 3/2004 | Clement et al. | |
| 6,771,596 B1 | 8/2004 | Angle et al. | |
| 6,840,938 B1 | 1/2005 | Morley et al. | |
| 6,849,071 B2 | 2/2005 | Whitman et al. | |
| 6,994,708 B2 | 2/2006 | Manzo | |
| 6,997,723 B2 | 2/2006 | Lee | |
| D517,501 S | 3/2006 | Kotyk | |
| 7,122,032 B2 | 10/2006 | Shinmura et al. | |
| 7,217,269 B2 | 5/2007 | El-Galley et al. | |
| 7,320,700 B2 | 1/2008 | Cooper et al. | |
| 7,353,068 B2 | 4/2008 | Tanaka et al. | |
| 7,367,973 B2 | 5/2008 | Manzo et al. | |
| 7,379,563 B2 | 5/2008 | Shamaie | |
| 7,428,439 B1 | 9/2008 | Reynolds et al. | |
| 7,594,912 B2 | 9/2009 | Cooper et al. | |
| 7,959,471 B2 | 6/2011 | Omori | |
| 8,052,470 B1 | 11/2011 | Lin | |
| 8,083,548 B1 | 12/2011 | Lin | |
| 8,120,301 B2 | 2/2012 | Goldberg et al. | |
| 8,398,541 B2 | 3/2013 | Dimaio et al. | |
| 8,398,634 B2 | 3/2013 | Manzo et al. | |
| 8,418,073 B2 | 4/2013 | Mohr et al. | |
| 8,423,182 B2 | 4/2013 | Robinson et al. | |
| 8,508,173 B2 | 8/2013 | Goldberg et al. | |
| 8,657,808 B2 | 2/2014 | Mcpherson et al. | |
| 8,852,208 B2 | 10/2014 | Gomez et al. | |
| 8,862,268 B2 | 10/2014 | Robinson et al. | |
| 9,259,283 B2 | 2/2016 | Ogawa et al. | |
| 9,301,811 B2 | 4/2016 | Goldberg et al. | |
| 9,375,288 B2 | 6/2016 | Robinson et al. | |
| 9,814,536 B2 | 11/2017 | Goldberg et al. | |
| 9,827,059 B2 | 11/2017 | Robinson et al. | |
| 10,575,909 B2 | 3/2020 | Robinson et al. | |
| 10,624,706 B2 | 4/2020 | Goldberg et al. | |
| 10,631,939 B2 | 4/2020 | Dachs, II et al. | |
| 10,864,048 B2 | 12/2020 | Holop et al. | |
| 11,071,595 B2 | 7/2021 | Johnson et al. | |
| 11,160,622 B2 | 11/2021 | Goldberg et al. | |
| 11,372,416 B2 | 6/2022 | Shalev-Shwartz et al. | |
| 11,540,883 B2 | 1/2023 | Moyer et al. | |
| 2001/0036245 A1 | 11/2001 | Kienzle et al. | |
| 2002/0049004 A1 | 4/2002 | Davis et al. | |
| 2002/0072736 A1 | 6/2002 | Tierney et al. | |
| 2002/0173799 A1 | 11/2002 | Besharim et al. | |
| 2003/0040204 A1 | 2/2003 | Chen et al. | |
| 2003/0135204 A1 | 7/2003 | Lee et al. | |
| 2003/0163029 A1 | 8/2003 | Sonnenschein et al. | |
| 2004/0024288 A1 | 2/2004 | Uchikubo | |
| 2004/0111183 A1 | 6/2004 | Sutherland et al. | |
| 2004/0152354 A1 | 8/2004 | Luther et al. | |
| 2004/0167515 A1 | 8/2004 | Petersen et al. | |
| 2005/0008043 A1 | 1/2005 | Kousek et al. | |
| 2005/0021021 A1 | 1/2005 | Foltz et al. | |
| 2005/0080403 A1 | 4/2005 | Takahashi | |
| 2005/0205288 A1 | 9/2005 | Fung et al. | |
| 2005/0251026 A1 | 11/2005 | Stone | |
| 2005/0251228 A1 | 11/2005 | Hamel | |
| 2006/0079889 A1 | 4/2006 | Scott et al. | |
| 2006/0087746 A1 | 4/2006 | Lipow | |
| 2006/0142657 A1 | 6/2006 | Quaid et al. | |
| 2007/0013336 A1 | 1/2007 | Nowlin et al. | |
| 2007/0016174 A1 | 1/2007 | Millman et al. | |
| 2007/0078539 A1 | 4/2007 | Kuhner et al. | |
| 2007/0167968 A1 | 7/2007 | Pandey | |
| 2007/0239172 A1 | 10/2007 | Lee et al. | |
| 2008/0046122 A1 | 2/2008 | Manzo et al. | |
| 2008/0107241 A1 | 5/2008 | Yatsenko et al. | |
| 2008/0125794 A1 | 5/2008 | Brock et al. | |
| 2008/0140158 A1 | 6/2008 | Hamel et al. | |
| 2008/0147089 A1 | 6/2008 | Loh et al. | |
| 2008/0183189 A1 | 7/2008 | Teichman et al. | |
| 2008/0217564 A1 | 9/2008 | Beyar et al. | |
| 2008/0221473 A1 | 9/2008 | Calancie et al. | |
| 2008/0249547 A1 | 10/2008 | Dunn | |
| 2008/0262538 A1 | 10/2008 | Danitz et al. | |
| 2008/0281301 A1 | 11/2008 | DeBoer et al. | |
| 2008/0319275 A1 | 12/2008 | Chiu et al. | |
| 2008/0319313 A1 | 12/2008 | Boivin et al. | |
| 2009/0009492 A1 | 1/2009 | Gregorio et al. | |
| 2009/0012533 A1 | 1/2009 | Barbagli et al. | |
| 2009/0024142 A1 | 1/2009 | Ruiz Morales | |
| 2009/0088774 A1 | 4/2009 | Swarup et al. | |
| 2009/0248041 A1 | 10/2009 | Williams et al. | |
| 2009/0254077 A1* | 10/2009 | Craig | A61B 18/1206 606/33 |
| 2009/0275940 A1* | 11/2009 | Malackowski | A61B 18/1233 606/42 |
| 2010/0082039 A1 | 4/2010 | Mohr et al. | |
| 2010/0121320 A1 | 5/2010 | Hosier et al. | |
| 2010/0191088 A1 | 7/2010 | Anderson et al. | |
| 2010/0228264 A1* | 9/2010 | Robinson | A61B 34/30 606/130 |
| 2010/0234857 A1 | 9/2010 | Itkowitz et al. | |
| 2010/0305427 A1 | 12/2010 | Huber et al. | |
| 2011/0079626 A1 | 4/2011 | Viola et al. | |
| 2011/0118752 A1 | 5/2011 | Itkowitz et al. | |
| 2011/0118753 A1 | 5/2011 | Itkowitz et al. | |
| 2011/0121049 A1 | 5/2011 | Malinouskas et al. | |
| 2011/0144636 A1 | 6/2011 | Alexander et al. | |
| 2011/0208185 A1 | 8/2011 | Diamant et al. | |
| 2011/0238079 A1 | 9/2011 | Hannaford et al. | |
| 2011/0276058 A1 | 11/2011 | Choi et al. | |
| 2011/0282140 A1 | 11/2011 | Itkowitz et al. | |
| 2011/0282141 A1 | 11/2011 | Itkowitz et al. | |
| 2012/0004655 A1 | 1/2012 | Kim et al. | |
| 2012/0046659 A1 | 2/2012 | Mueller | |
| 2012/0071891 A1 | 3/2012 | Itkowitz et al. | |
| 2012/0071892 A1 | 3/2012 | Itkowitz et al. | |
| 2012/0116381 A1 | 5/2012 | Houser et al. | |
| 2012/0180751 A1 | 7/2012 | Tuerk et al. | |
| 2012/0232540 A1 | 9/2012 | Baur et al. | |
| 2012/0310241 A1 | 12/2012 | Orszulak | |
| 2013/0053840 A1 | 2/2013 | Krapohl et al. | |
| 2013/0274734 A1 | 10/2013 | Maass et al. | |
| 2013/0304256 A1 | 11/2013 | Moll et al. | |
| 2014/0128886 A1 | 5/2014 | Holop et al. | |
| 2014/0180272 A1 | 6/2014 | Dachs, II et al. | |
| 2015/0012134 A1 | 1/2015 | Robinson et al. | |
| 2015/0018622 A1 | 1/2015 | Tesar et al. | |
| 2020/0246092 A1 | 8/2020 | Robinson et al. | |
| 2020/0253672 A1 | 8/2020 | Dachs, II et al. | |
| 2020/0281672 A1 | 9/2020 | Goldberg et al. | |
| 2021/0169592 A1 | 6/2021 | Robinson et al. | |

FOREIGN PATENT DOCUMENTS

| | | |
|---|---|---|
| CN | 102723645 A | 10/2012 |
| CN | 102727302 A | 10/2012 |
| EP | 2138105 A2 | 12/2009 |
| JP | 2001314411 A | 11/2001 |
| JP | 2004208922 A | 7/2004 |
| JP | 2006255395 A | 9/2006 |
| JP | 2009544422 A | 12/2009 |
| JP | 2011506008 A | 3/2011 |
| JP | 2011104379 A | 6/2011 |
| JP | 2012169273 A | 9/2012 |
| JP | 2012210294 A | 11/2012 |
| JP | 2017513552 A | 6/2017 |

(56) References Cited

FOREIGN PATENT DOCUMENTS

| WO | WO-9749340 A1 | 12/1997 |
|---|---|---|
| WO | WO-2007075864 A1 | 7/2007 |
| WO | WO-2008098085 A2 | 8/2008 |
| WO | WO-2010008126 A1 | 1/2010 |
| WO | WO-2011060139 A2 | 5/2011 |
| WO | WO-2011125007 A1 | 10/2011 |
| WO | WO-2015142814 A1 | 9/2015 |

OTHER PUBLICATIONS 802.3af-2003—IEEE Standard for Information Technology—Telecommunications and Information Exchange Between Systems—Local and Metropolitan Area Networks—Specific Requirements [online], 2003, Current Version Jul. 22, 2003, DOI 10.1109/IEEESTD 2003.94284, Persistent Link: http://ieeexplore.ieee.org/servlet/opac?punumber=8612.
Applied Surgical, Data Sheet for Gemini Operating Room, 1 Page, 2006; Internet: http://appliedsurgicalsolutions.com/.
Communication dated Mar. 12, 2018, received from the European Patent Office in European Patent Application No. 13851407.0 (6 pages).
Dugan, Kelli M., "Stepping Out," Birmingham Business Journal, Mar. 24, 2006, 2 pages; Internet: http://www.oadi.org/client%20news/Applied%20Surgical%20032406.pdf.
Erickson, J.R. et al., "Connectors Take on a new Life," Published Online on Sep. 1, 2012, URL: http://www.designworlddonline.com/connectors-take-on-a-new-life/.
Harris, William, "How Haptic Technology Works," downloaded Oct. 24, 2008, 6 pages; Internet: http://electronics.howstuffworks.com/gadgets/other-gadgets/haptic-technology4.htm.
International Search Report and Written Opinion for Application No. PCT/US2013/059938, mailed on Dec. 10, 2013, 11 pages.
International Search Report and Written Opinion for Application No. PCT/US2013/068059, mailed on Feb. 11, 2014, 18 pages.
Linemaster Switch Corp., Brochure titled "Precision Begins with a Linemaster Switch," 8 pages, 2000.
Linemaster Switch Corp., Data Sheet for Linemaster Wireless Linear Foot Switch, Lit-002 Rev D, 2 pages, downloaded Jan. 2, 2009; Internet: http://www.linemaster.com/media/DataSheets/LIT-002%20Rev%20Dsm.pdf.
Linemaster Switch Corp., Information sheet for Linemaster Infrared Wireless Linear Foot Switch, 2 pages, downloaded Jan. 2, 2009; Internet: http://www.linemaster.com/wirelesslinear.shtml.
Medical Design Magazine, "Wireless Footswitch Controls Several Surgical Devices," Nov. 1, 2006, 1 page; Internet: http://medicaldesign.com/engineering-prototyping/wireless_footswitch_controls/index.html.
Office Action mailed May 8, 2017 for Chinese Application No. 201380057047.5 filed Nov. 1, 2013, 14 pages.
PCT/US10/26307 International Search Report and Written Opinion of the International Searching Authority, mailed Jul. 22, 2010, 9 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Wikipedia, entry on "Ergonomics," printed Feb. 24, 2009 at 11:24 p.m., 10 pages; Internet: http://en.wikipedia.org/wiki/Ergonomics.
Erickson J.R., "Connectors Take on a New Life," Colder Products Company, Sep. 2012, 1 page.

* cited by examiner

FLUX DISAMBIGUATION FOR TELEOPERATED SURGICAL SYSTEMS

CROSS-REFERENCE TO RELATED APPLICATIONS

This application is a divisional application of U.S. application Ser. No. 14/070,184, filed Nov. 1, 2013, which claims the benefit of U.S. Provisional Application No. 61/721,909, filed Nov. 2, 2012, which is incorporated by reference herein in its entirety.

TECHNICAL FIELD

The present disclosure relates to surgical instruments for robotic (teleoperated) surgical systems, and related systems, devices and methods for controlling delivery of a flux supplied from an external source to such instruments. In particular, the present disclosure relates to systems, devices, and methods for controlling energy delivery to surgical instruments, such as electrosurgical instruments, of teleoperated surgical systems.

INTRODUCTION

Some minimally invasive surgical techniques are performed remotely through the use of robotically-controlled (teleoperated) surgical instruments. In teleoperated surgical systems, surgeons provide input commands, e.g., via manipulation of input devices, at a surgeon side console. Those inputs are passed via a controller (e.g., one or more processors) to a patient side cart that interfaces with one or more teleoperated surgical instruments. Based on the surgeon's inputs at the surgeon side console, the one or more teleoperated surgical instruments are actuated at the patient side cart to operate on the patient, thereby creating a master-slave control relationship between the surgeon side console and the surgical instrument(s) at the patient side cart.

Various surgical procedures can be performed using teleoperated surgical systems, some of which require the delivery of a flux supplied from an external source to the patient via a surgical instrument at the patient side cart. For example, cauterization (e.g., including tissue ablation, tissue sealing, tissue cutting etc.) is used in many teleoperated surgical procedures. Electrosurgical instruments can be used to deliver an electrical energy flux for cautery procedures in teleoperated surgical systems. Such instruments include, but are not limited to, both bipolar configurations wherein the end effector of the instrument that delivers the cautery electrical energy comprises two electrodes with one being the source of the supplied current and the other being the sink; monopolar configurations wherein the current is delivered from a single end effector electrode and through the patient to a ground electrode outside of the patient's body; and mixed mode configurations wherein the instrument can deliver both bipolar and monopolar energy. Some exemplary bipolar electrosurgical instruments have jawed end effector structures, including, but not limited to, for example, vessel sealers, clamps, and forceps. Some exemplary monopolar electrosurgical instruments have a single finger end effector structures, including, but not limited to, for example, spatulas, and hooks. Those having ordinary skill in the art will appreciate that jawed end effector structures also can be configured as monopolar by delivering monopolar cautery energy through only one of the jaws, again with the use of an external ground electrode. Scissors are an example of jawed end effector structures that can be configured as either monopolar (in which only one blade of the pair delivers electrical energy) or bipolar.

Other types of surgical instruments also can be configured to have a flux delivered thereto from an external supply source. For example, aside from an electrical energy flux, other energy fluxes such as, for example, ultrasound, laser, and/or other light energy, can be delivered to the patient through surgical instruments mounted at the patient side cart. Yet other examples of fluxes that can be delivered to surgical instruments include fluid, such as, for example, irrigation, or vacuum pressure.

The patient side cart of a teleoperated surgical system generally has one or more manipulator arms that hold various surgical instruments to be used during a procedure. Electrosurgical instruments, and others that deliver fluxes from an external source to the patient, are somewhat unique in that, in addition to being coupled to various actuation interface mechanisms at the patient side cart to control movement of the instrument based on the master inputs, they also may be in communication with a flux generation source, e.g., an electrical energy generation source in communication with an electrosurgical instrument. As with the movement of the instrument in general, flux delivery from such a surgical instrument to the patient can be responsive to an input command (e.g., pressing of a foot pedal or other input device) generated at the surgeon side console.

It may be desirable for various reasons to have more than one surgical instrument for flux delivery (e.g., more than one electrosurgical instrument) mounted at the patient side cart during a teleoperated surgical procedure. A need exists, however, to provide a teleoperated surgical system that can reliably and in an automated manner determine which one(s) of a plurality of surgical instruments mounted at a patient side cart is in communication with an external flux supply source, such as, for example, an energy generator. There also exists a need to provide various control schemes and automated control methods relating to flux delivery to surgical instruments of teleoperated surgical systems. Further, there exists a need to manage flux supply to such instruments in ambiguous conditions where it may be uncertain which instrument will be activated upon a flux input command at the surgeon side console. A need also exists to enhance safety of teleoperated surgical systems in controlling flux supply to instruments.

SUMMARY

Various exemplary embodiments disclosed herein may solve one or more of the above-mentioned problems and/or may demonstrate one or more of the above-mentioned desirable features. Other features and/or advantages may become apparent from the description that follows.

In accordance with at least one exemplary embodiment, the present disclosure contemplates a method comprises receiving a first signal at a controller of a teleoperated surgical system indicating that a surgical instrument is in an installed position at a patient side cart of the teleoperated surgical system, receiving a second signal at the controller indicating that the surgical instrument is in a flux connection state, and outputting a signal via the controller to provide feedback indicating that the surgical instrument is in the flux connection state.

A method in accordance with yet another exemplary embodiment of the disclosure can include receiving at a controller of a teleoperated surgical system at least one signal indicating which of a plurality of surgical instruments positioned at a patient side cart of the teleoperated surgical system are in an energy connection state and controlling energy transmission to the surgical instruments based on which of the plurality of installed surgical instruments are in the energy connection state. Receiving the at least one signal regarding which of the plurality of surgical instruments are in the energy connection state may comprise receiving a plurality of signals indicating that more than one of the plurality of installed surgical instruments are in the energy connection state. The controlling the energy transmission may comprise prohibiting or permitting energy transmission to the plurality of installed surgical instruments based on energy type of the plurality of installed surgical instruments in the energy connection state.

In yet another exemplary embodiment in accordance with the present disclosure, a surgical instrument for a teleoperated surgical system can include a housing for coupling the surgical instrument in an installed position at a patient side cart of a teleoperated surgical system, the housing comprising a connector feature for engagement with a flux transmission conduit. The surgical instrument can further include a mechanism that is transitionable between a first state in which the connector feature and the flux transmission conduit are in disengagement and a second state in which the connection feature and the flux transmission conduit are in engagement. In the installed position of the surgical instrument, a transition between the first and second states of the mechanism is detectable by a sensor.

In yet another exemplary embodiment, the present disclosure contemplates a system for detecting an operative condition of a surgical instrument of a teleoperated surgical system. The system can include a surgical instrument comprising a housing for coupling the surgical instrument in an installed position at a patient side cart of a teleoperated surgical system, the housing comprising a connector feature. The system can further include a flux transmission conduit engageable with the connector feature to place the surgical instrument in a flux connection state, and a sensing device associated with the patient side cart and disposed to detect a presence of the flux transmission conduit in a flux connection state of the surgical instrument.

Additional objects, features, and/or advantages will be set forth in part in the description which follows, and in part will be obvious from the description, or may be learned by practice of the present disclosure. At least some of the objects, features, and/or advantages will be realized and attained by means of the elements and combinations particularly pointed out in the appended claims.

It is to be understood that both the foregoing general description and the following detailed description are exemplary and explanatory only and are not restrictive of the invention, as claimed; the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

Figure 1:
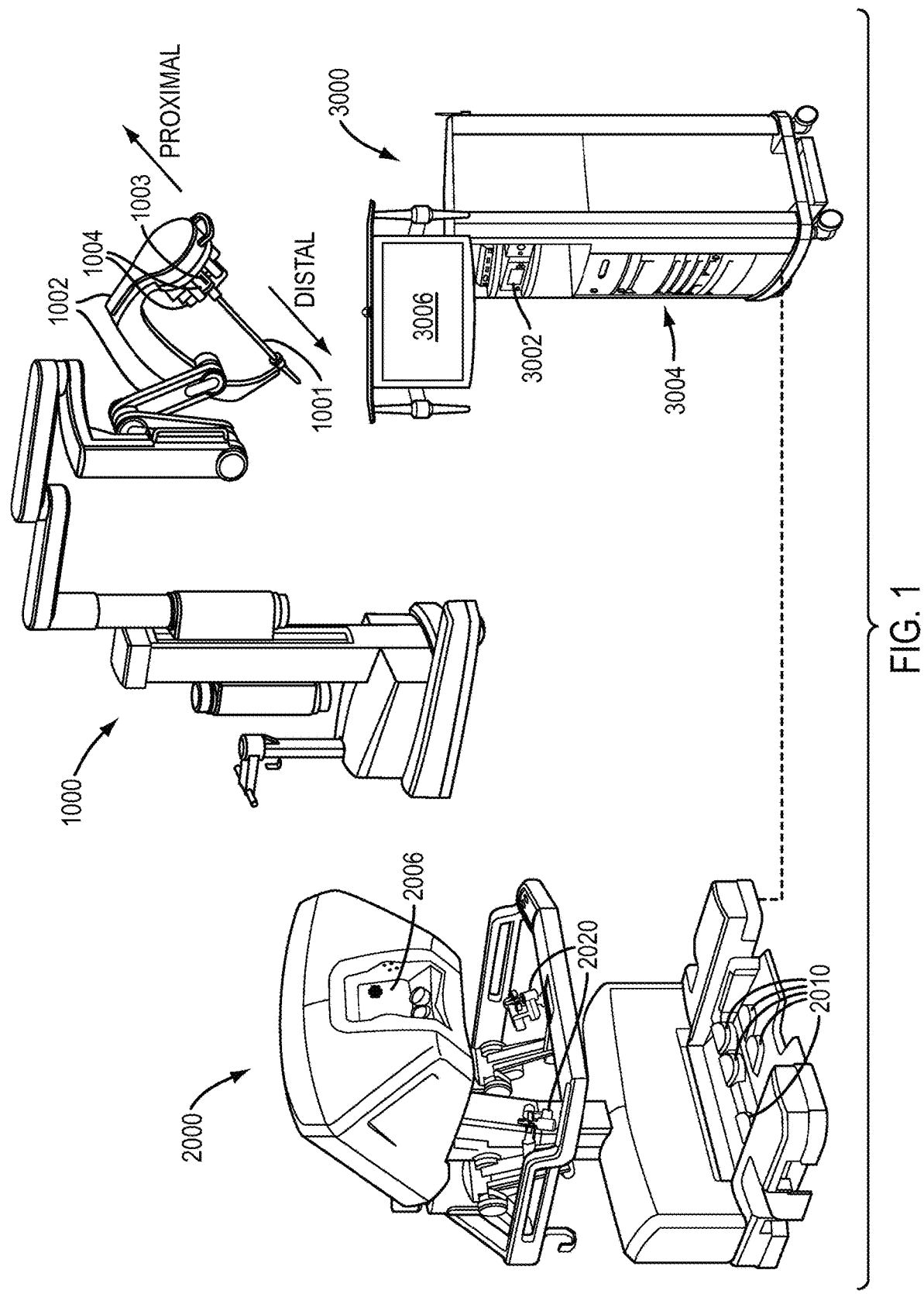
FIG. 1 is a diagrammatic view of various components of an exemplary teleoperated surgical system in accordance with the present disclosure.

This description and the accompanying drawings that illustrate exemplary embodiments should not be taken as limiting, with the claims defining the scope of the present disclosure, including equivalents. Various mechanical, compositional, structural, electrical, and operational changes may be made without departing from the scope of this description and the invention as claimed, including equivalents. In some instances, well-known structures and/or techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Although for ease of description various exemplary embodiments set forth below describe electrosurgical instruments, electrical energy generators, and the delivery of electrical energy (e.g., cautery energy), those having ordinary skill in the art will appreciate that the present disclosure can be applied to a variety of surgical instruments that are provided with any type of flux (e.g., other energy flux, such as laser, ultrasound, or nerve stimulation; a fluid flux; a vacuum pressure flux, etc.) by a remotely controlled, external flux generator or other flux supply source to deliver the desired flux to a patient for use in performing or observing a surgical procedure. As used herein, the term "flux" may be defined as a flow useful in surgical operations that is transmitted from one source to another source, for example, between a flux supply source and a flux delivery component, such as, for example, an electrosurgical instrument (e.g., to be delivered to a patient via end effector thereof).

Nonlimiting examples of various fluxes for which the present disclosure can be applied with appropriate modification to components using or transmitting the flux, as those of ordinary skill in the art would appreciate, include but are not limited to, for example, electrical energy (e.g., cautery or nerve stimulation energy), laser energy, ultrasound energy, light energy, or radio frequency energy; fluids (e.g., for irrigation or insufflation); vacuum pressure (in which case a negative pressure flux from a "source" is "supplied" to the instrument) to surgical instruments; and image and/or audio streams. Nonlimiting examples of external flux supply sources may include, for example, energy generators, fluid delivery sources, gas supply sources, vacuum sources, etc. By way of nonlimiting example, as will be appreciated by those of ordinary skill in the art, laser energy can be delivered via a fiber optic transmission cable from a laser energy generator to a surgical instrument having an end effector configured to deliver the laser energy to the patient.

Thus, it will be appreciated by one of ordinary skill in the art that the systems and methods described herein with reference to electrosurgical instruments and the delivery of electrical energy can be used in conjunction with other remotely controlled surgical instruments supplied with remotely delivered fluxes from one or more flux generation sources. Transmission of the flux from the flux generation source to the surgical instrument can be via a flux transmission conduit, such as, for example, an energy transmission cable, a hose, a fiber optic cable, etc., configured to be connected to the surgical instrument at one end and to the external flux supply source at the other end.

As a safety precaution, some existing surgical systems prohibit the supply of energy (e.g., electrical energy) to instruments installed at the patient side cart if more than one energy delivery surgical instrument is installed. This is because an ambiguity exists regarding which instrument will be activated when an energy input command (e.g., a cautery command) is provided at the surgeon side console. Such prohibition, however, can limit the options available to the surgeon during a surgical procedure and the configuration flexibility of the overall surgical system. For example, it may be desirable to have two electrosurgical instruments installed at the patient side cart, one of which can be used for ordinary grasping and one of which can be used for both grasping and cautery procedures. Installing instruments that have such multiple functionality (e.g., delivering energy and/or grasping as desired) also can permit fewer instrument changes, thereby reducing the overall number of instruments that may need to be stocked. In addition, in certain surgical procedures, it may be desirable to install electrosurgical instruments of differing types, e.g., monopolar and bipolar, based on a requirement of differing cautery operations that may be desired.

Various exemplary embodiments provide a robust way for the teleoperated surgical system to determine which one or ones of a plurality of surgical instruments (e.g., electrosurgical instruments) that are installed at a patient side cart are in flux communication (e.g., energy communication) with one or more external flux supply sources (e.g., energy generator (s)). According to various exemplary embodiments, the determination can be made at a controller based on receipt of a signal indicative of a flux transmission conduit being engaged (e.g., an energy transmission cable in electrical connection) with one or more of the installed electrosurgical instruments. Information regarding the determination of which instrument is in flux communication with a flux generator can be shared with the surgeon so that the surgeon knows that if a particular master flux input command at the surgeon side console is provided, which surgical instrument is expected to be activated, e.g., to perform a surgical procedure that uses the delivery of the transmitted flux.

Various exemplary embodiments also contemplate controlling the delivery of a flux, such as, electrical energy, based on the determination information. For example, various exemplary embodiments contemplate prohibiting a flux supply source from sending a flux to one or more electrosurgical instruments upon certain ambiguous conditions of the teleoperated surgical system with respect to which surgical instrument will be activated upon a flux input command at the surgeon side console.

Various exemplary embodiments described herein also provide the ability of the teleoperated surgical system to confirm that an instrument is in an installed position at the patient side cart, e.g., as opposed to being in close proximity or coupled to, but not in an accurately installed position.

In accordance with various exemplary embodiments, therefore, teleoperated surgical systems can in an automated and accurate manner track which installed surgical instruments (e.g., electrosurgical instruments) have flux transmission conduits (e.g., electrical energy transmission cables) connected thereto, confirm the correct installation of the instruments, provide feedback at the surgeon side console to share the information, and control the overall delivery of flux (e.g., electrical energy) to the instruments from a flux supply source (e.g., energy generator) based on the tracking information and master input commands at the surgeon side console. Such automated tracking and control features can, among others, enhance the safety of operation of the teleoperated surgical systems, reduce time spent and potential human error associated with manually tracking the information, reduce time spent in changing instruments at the patient side cart during a procedure that may benefit from the use of two electrosurgical operations by differing instruments, and/or provide greater flexibility in the types of surgical procedures that can be performed and the types of instruments that can be installed at the patient side cart at a time.

With reference now to the diagrammatic view of FIG. 1, various components of a minimally invasive teleoperated surgical system are illustrated. In exemplary embodiments, the teleoperated surgical system can be used to perform minimally invasive surgical procedures by interfacing with and controlling a variety of remotely operable surgical instruments 1001 (one such instrument 1001 being depicted), as those of ordinary skill in the art are generally familiar. The surgical instruments 1001 may be selected from a variety of instruments that are configured to perform various surgical procedures, and in accordance with various exemplary embodiments can be flux delivery surgical instruments such as electrosurgical instruments, for example, bipolar, monopolar, and/or mixed mode electrosurgical instruments.

As illustrated in FIG. 1, the teleoperated surgical system includes a patient side cart 1000, a surgeon side console 2000, and a control cart 3000 (sometimes referred to as an auxiliary or vision control cart). Those having ordinary skill in the art will appreciate that the system components in FIG. 1 are not shown in any particular positioning and can be arranged as desired, with the patient side cart 1000 being disposed relative to the patient so as to effect surgery on the patient. Those having ordinary skill in the art will appreciate, however, that it is contemplated within the scope of the present disclosure that exemplary embodiments can be implemented in a variety of surgical systems having a variety of configurations. For example, it is envisioned that various exemplary embodiments described herein could be used in conjunction with da Vinci® Surgical Systems. Further, reference is also made to U.S. Application Publication No. US 2011/0282358 A1 (published Nov. 17, 2011; entitled "SURGICAL SYSTEM INSTRUMENT MOUNTING") for a nonlimiting exemplary embodiment of a teleoperated surgical system architecture with which various exemplary embodiments herein can be used.

In general, the surgeon side console 2000 receives inputs from a user, e.g., a surgeon, by various input devices, including but not limited to, gripping mechanisms 2020 and foot pedals 2010, and serves as a master controller by which the patient side cart 1000 acts as a slave to implement the desired motions of the surgical instrument(s) 1001 interfaced therewith, in order to perform a surgical procedure. The surgeon side console 2000 also can include a viewer or display 2006 that allows the surgeon to view a three-dimensional image of the surgical site, for example, during the surgical procedure, e.g., via an optical endoscope at the patient side cart 1000. Although in various exemplary embodiments, one or more input mechanisms 2010, 2020 may be integrated into the surgeon side console 2000, various other input mechanisms may be added separately and provided so as to be accessible to the surgeon during use of the system, but not necessarily integrated into the surgeon side console 2000. In the context of the present disclosure, such additional input mechanisms are considered part of the surgeon side console.

Thus, a "surgeon side console" as used herein includes a console that comprises one or more input devices that a surgeon can manipulate to transmit signals, generally through a control cart described in more detail below, to actuate a surgical instrument interfaced with a patient side cart, and one or more output devices that can provide feedback to the surgeon. As used herein, it should be understood that a surgeon side console can include a unit (e.g., substantially as shown at 2000 in FIG. 1) that integrates the various input and output devices, with, for example, a display. However, the surgeon side console also can include separate input and/or output devices that are in signal communication with the control cart and accessible by a surgeon, although not necessarily integrated within a unit with various other input devices. As an example, in various exemplary embodiments input may be provided directly at the control cart 3000 and may provide input signals to a processor at the control cart. As such, a "surgeon side console" does not necessarily require all of the input and output devices to be integrated into a single unit and can include one or more separate input and/or output devices.

Figure 12:
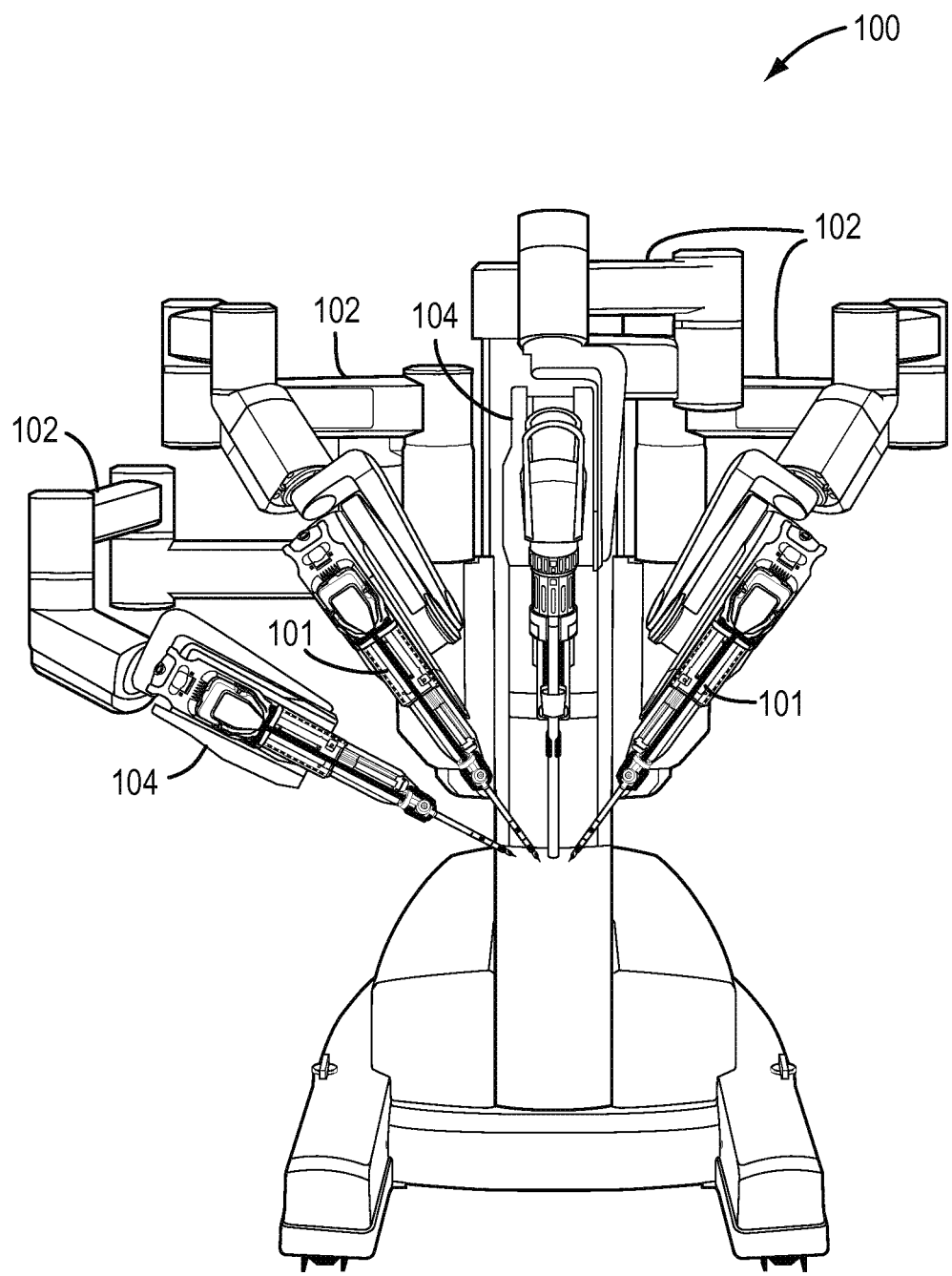
FIG. 12 is a diagrammatic view of another exemplary embodiment of a patient side cart in accordance with the present disclosure.

The patient side cart 1000 includes one or more jointed, positionable manipulator arms 1002 (the exemplary embodiment of FIG. 1 having only one such arm) configured to hold and manipulate various tools, including, but not limited to, for example, surgical instruments 1001. The patient side cart 1000 can control the surgical instruments 1001 via actuation interface assemblies 1004 mounted on the manipulator arm 1002 and configured to engage with transmission mechanisms provided at a proximal end of the surgical instruments 1001. The "proximal" and "distal" directions are shown in FIG. 1 relative to the surgical instrument. Based on the commands input at the surgeon side console 2000, the patient side cart 1000 can, through the actuation interfaces 1004 and transmission mechanisms, position and actuate the instrument(s) 1001 to perform a desired surgical procedure. Although the exemplary embodiment of FIG. 1 illustrates a single manipulator arm 1002 that can support multiple surgical instrument actuation interface assemblies 1004 and consequently multiple surgical instruments, those having ordinary skill in the art will appreciate that other patient side cart configurations, including for example patient side carts having multiple, independently movable manipulator arms each holding a differing surgical instrument, may be used and are considered as within the scope of the present disclosure. One exemplary embodiment of such a patient side cart 100 having a plurality of independently moveable manipulator arms 102 carrying actuation interface assemblies 104 that interface to actuate surgical instruments 101 is depicted in FIG. 12.

The control cart 3000 receives and transmits various control signals to and from the patient side cart 1000 and the surgeon side console 2000, and can transmit light and process images (e.g., from an endoscope at the patient side cart 1000) for display, such as, e.g., at display 2006 at the surgeon side console 2000 and/or on a display 3006 associated with the control cart 3000. Those having ordinary skill in the art are generally familiar with such teleoperated surgical systems.

In exemplary embodiments, the control cart 3000 may have all control functions integrated in a control processing unit, which can include a core processor, of the control cart 3000, or control functions may be distributed throughout the system among a core processor and the patient side cart and/or the surgeon side console. For simplicity, a single control processing unit 3004 with a core processor is depicted and referred to herein as a controller at control cart 3000. As shown in FIG. 1, additional control processing units may be provided as separate units and supported (e.g., in shelves) on the control cart 3000 for convenience. The latter may be useful, for example, when retrofitting existing control carts to control surgical instruments requiring additional functionality, for example, by providing electrical energy for use in monopolar and/or bipolar applications. For example, in various exemplary embodiments, one or more energy generators 3002 (sometimes referred to as electrosurgical units or ESUs), which generate and provide the energy to be transmitted to a surgical instrument used for energy delivery to a patient, may be provided as units separate from the core processor and supported on the control cart 3000 and in communication with the controller 3004 of the control cart 3000, or one or more of the energy generators 3002 may be incorporated as an integrated part of the control cart 3000 and core processor. In various exemplary embodiments, in the case of electrosurgical energy generators for example, one or more electrical energy generators can be used to provide monopolar and/or bipolar energy, and which energy is provided to an electrosurgical instrument (for example, which energy generator unit will be controlled to deliver a particular energy type) can be controlled based on mapping particular input devices (e.g., pedals) at the surgeon side console to particular energy types (e.g., bipolar or monopolar).

Accordingly, as used herein, the term "controller" and variations thereof should be understood to include one or more controllers (e.g., processors, such as core processor for controlling overall system functionality) that receive, processes and transmit signals to and from the patient side cart 1000 and surgeon side console 2000, as well as to and from one or more energy generators that provide energy to be delivered by an electrosurgical instrument. In accordance with various exemplary embodiments, a control cart as used herein also can include one or more controllers that are provided in direct signal communication with one or more of the surgical instruments 1001 as well. As such, a "control cart" or "controller" does not necessarily require all control processing units to be integrated into a single unit and can include one or more separate control processing units functionally dependent on each other, with various processing functions and capabilities distributed through the entire teleoperated surgical system. Such separate control processing units can be useful to add functionality to operational aspects of a surgical instrument without necessarily having to rely on servo actuators associated with the patient side cart. Such control processing units can also be useful when retrofitting existing teleoperated surgical system as a way to increase control functionality and signal processing into the electronics/control cart.

Figure 2:
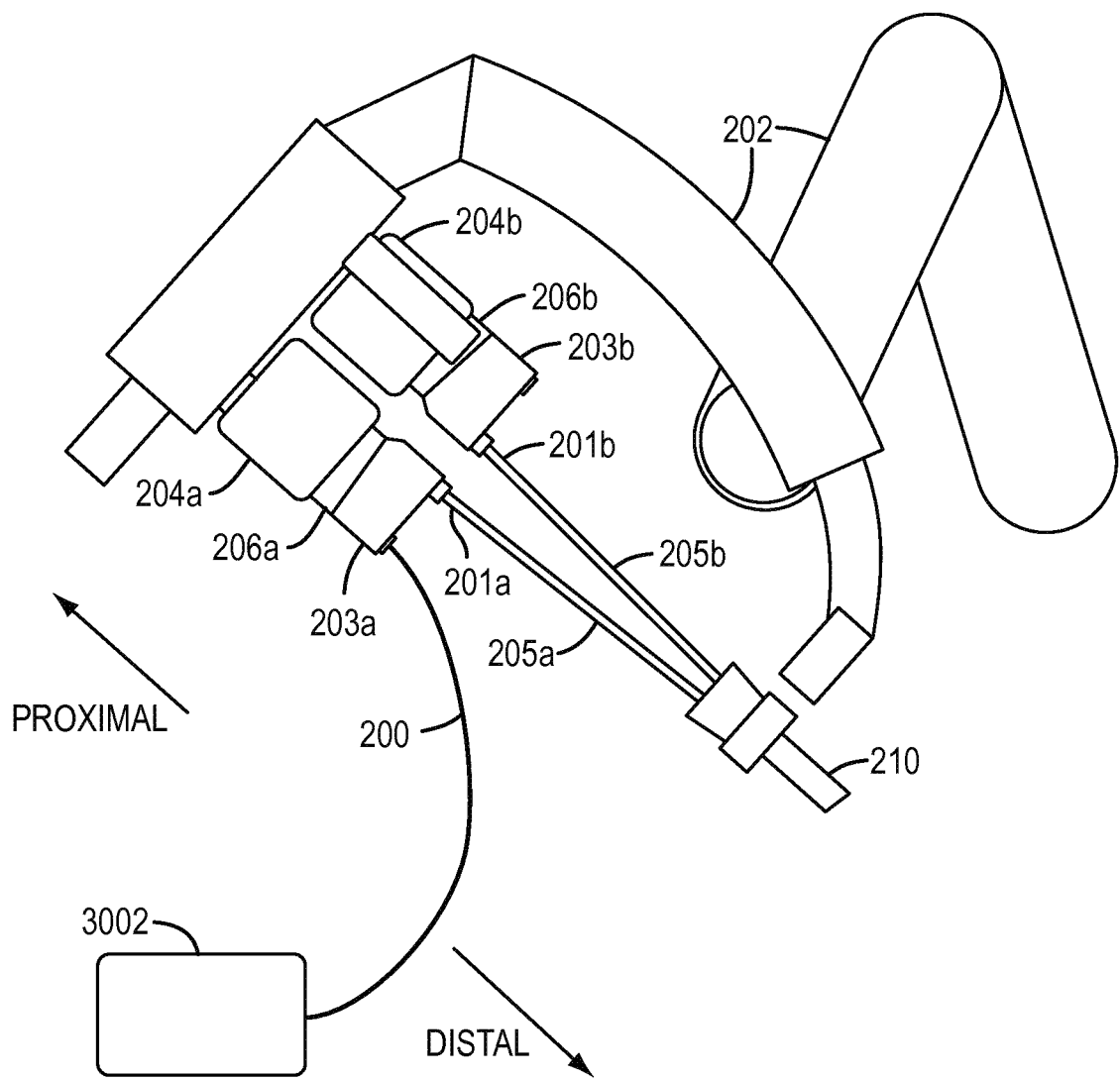
FIG. 2 is a partial schematic view of an exemplary embodiment of a manipulator arm of a patient side cart with two electrosurgical instruments in an installed position, one of which is shown in electrical communication with a flux generator.

Referring now to the schematic illustration of FIG. 2, a portion of an exemplary embodiment of a manipulator arm 202 of a patient side cart with two surgical instruments 201A, 201B in an installed position is shown. The schematic illustration of FIG. 2 depicts only two surgical instruments for simplicity, but more than two surgical instruments may be received in an installed position at a patient side cart as those having ordinary skill in the art are familiar with. As described above, each surgical instrument 201A, 201B includes an instrument shaft 205A, 205B that at a distal end has a moveable end effector (not shown in FIG. 2), and may or may not include a wrist mechanism (also not shown in FIG. 2) to control the movement of the end effector. Persons of ordinary skill in the art are familiar with a variety teleoperated, minimally invasive surgical instruments with end effectors and/or wrist mechanisms and details regarding those components are not the focus of the present disclosure.

In the exemplary embodiment of FIG. 2, the distal end portions of the surgical instruments 201A, 201B are received through a single port structure 210 to be introduced into the patient. Other configurations of patient side carts that can be used in conjunction with the present disclosure can use several individual manipulator arms on which each surgical instrument is installed, for example as depicted in the exemplary embodiment of FIG. 12.

Transmission housings 203A, 203B are disposed at a proximal end of each shaft 205A, 205B and connect through a sterile adaptor 206A, 206B with actuation interface assemblies 204A, 204B. As discussed above, the actuation interface assemblies 204A, 204B contain a variety of drive mechanisms (not depicted in FIG. 2) that are controlled by a controller (e.g., at the control cart 3000) to respond to input commands at the surgeon side console 2000. Those drive mechanisms in turn interface and act upon various force transmission mechanisms housed in the transmission housings 203A, 203B to transmit forces along the shafts 205A, 205B and to the end effectors/wrists of the instruments 201A, 201B to provide multiple degrees of freedom (DOF) movement thereto, including for example, roll of the shaft, Cartesian yaw and pitch movements of the end effector and/or wrist, opening/closing of jawed end effectors, and/or translation of the surgical instrument and/or components at the end effector. As those of ordinary skill in the art will appreciate and are familiar with, the various DOF movements effected depend upon the type of surgical instrument installed.

In various exemplary embodiments, at least one of the surgical instruments 201A is in communication via a flux transmission conduit 200 with a flux source 3002 such that when the surgeon (e.g., at a surgeon side console 2000) provides a flux input command during a surgical procedure, a controller (e.g., at the control cart 3000) sends a signal to the flux source 3002 and the surgical instrument 201A is activated by flux supplied from the flux source 3002 through the flux transmission conduit 200. In various exemplary embodiments, the surgical instruments 201A, 201B are electrosurgical instruments, the flux transmission conduit 200 is an electrical energy transmission cable, and the flux source 3002 is an electrical energy generator. Thus, when the surgeon (e.g., at a surgeon side console 2000) inputs a command for electrical energy during a surgical procedure (e.g., a cautery command such as by pressing a pedal 2010), a signal I sent via the controller 3004 (e.g., at control cart 3000 or otherwise distributed across the various teleoperated surgical system components) to the electrical energy generator 3002. This in turn activates the electrosurgical instrument 201A by electrical energy supplied from the electrical energy generator 3002 through the electrical connection cable 200.

As discussed above, various exemplary embodiments of a teleoperated surgical system contemplate the ability to determine which of a plurality of surgical instruments that are in installed positions (e.g., transmission mechanisms and actuation interface assemblies engaged) at a patient side cart are in communication with a flux source by detecting the presence of an flux transmission conduit connected to a respective instrument. Such detection can be accomplished using various sensing mechanisms, various exemplary embodiments of which are described in further detail below.

Thus, with reference again to FIG. 2, a teleoperated surgical system in accordance with at least one exemplary embodiment, can determine that an electrosurgical instrument 201A is in electrical communication with the electrical energy generator 3002 via the detection of the electrical energy transmission cable 200 being connected to the electrosurgical instrument 201A. Based on such detection, various control schemes can be implemented and/or information regarding the same can be provided as feedback, for example, to a surgeon.

Figure 3A:
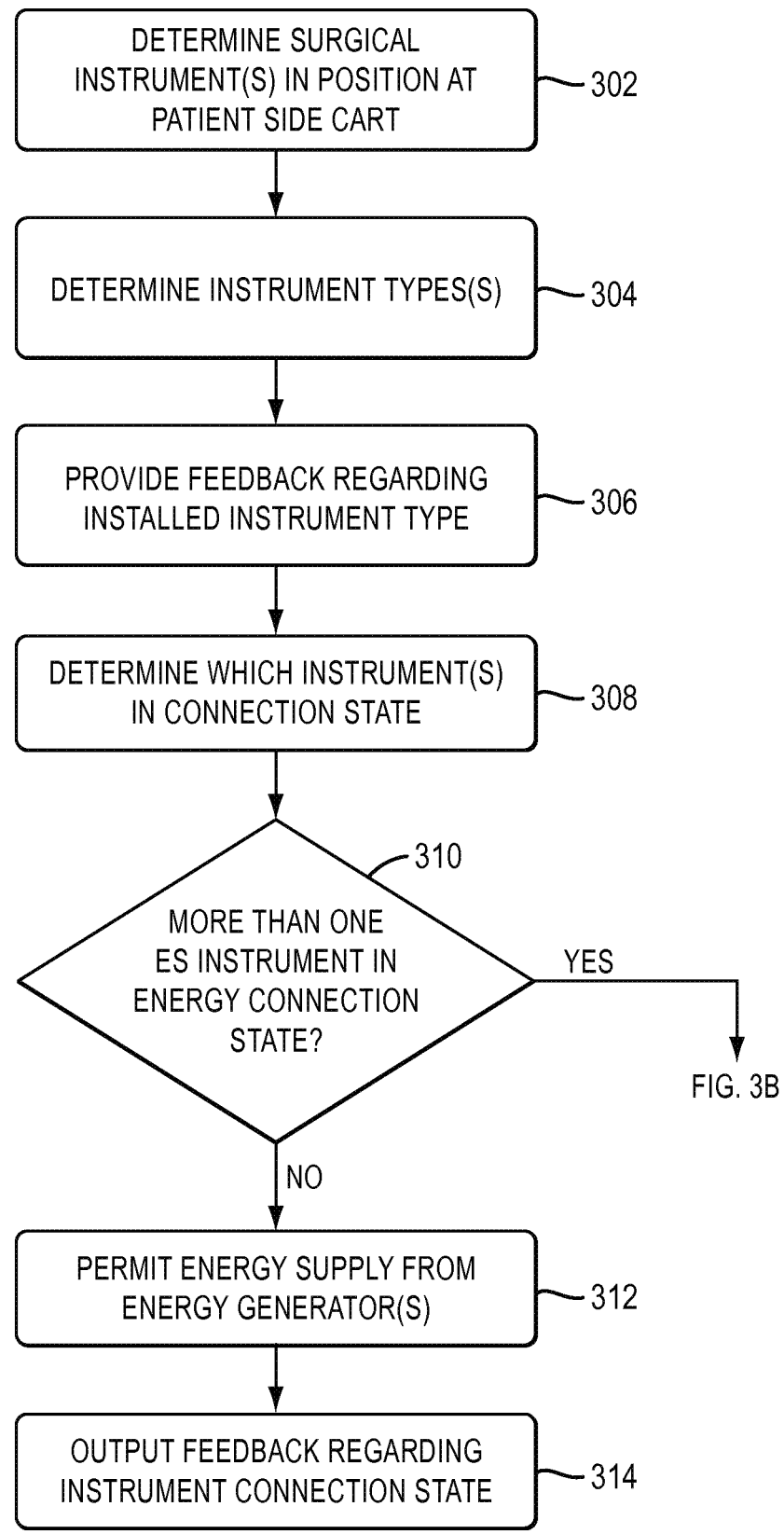
FIGS. 3A and 3B are flow diagrams illustrating exemplary workflow components in accordance with various exemplary embodiments of the present disclosure.
Figure 3B:
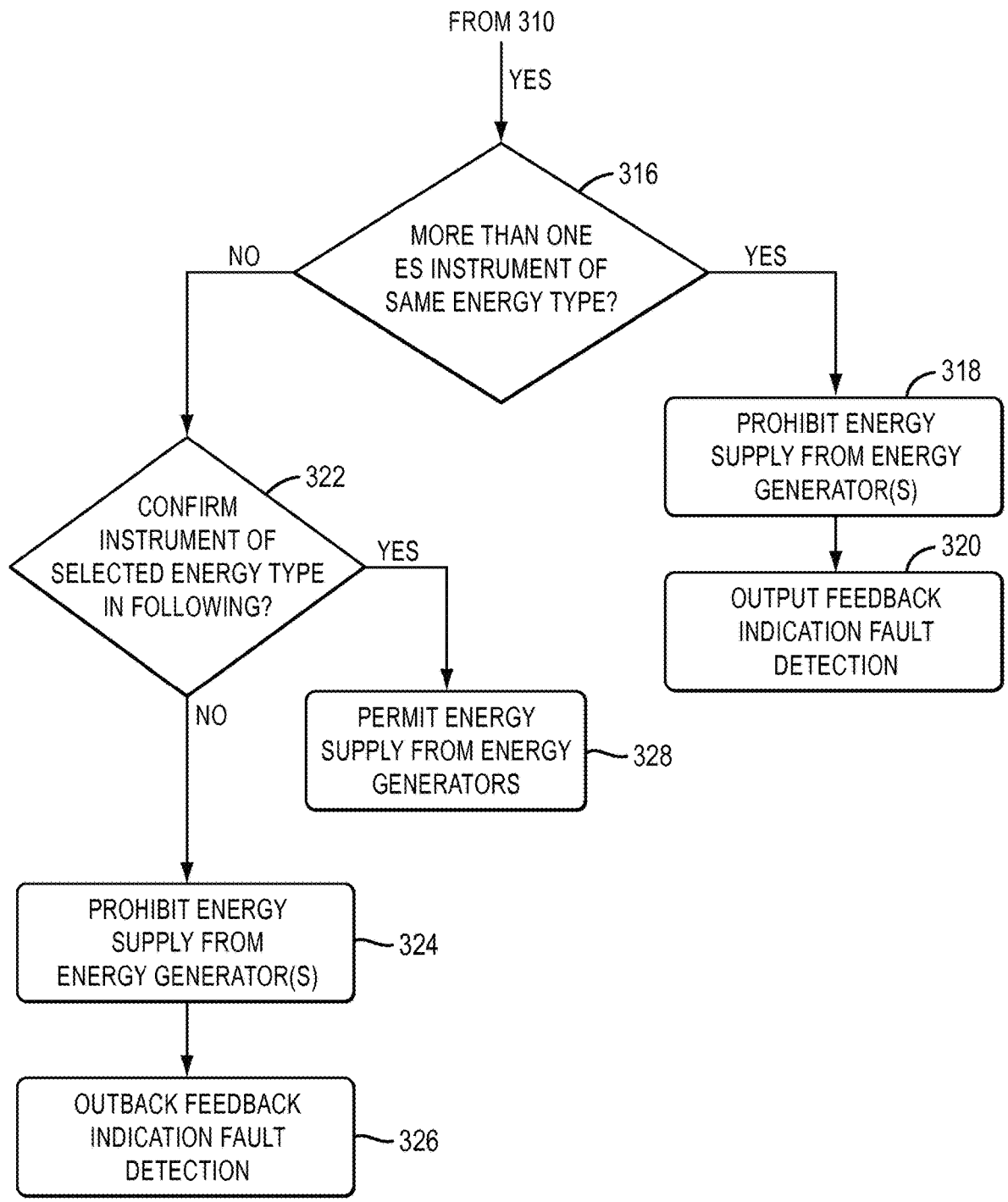

A flow diagram that depicts exemplary steps of a workflow in accordance with various exemplary embodiments is shown in FIGS. 3A and 3B. It should be understood that each of the steps depicted may not be required in any particular embodiment and some of the steps depicted may occur in other orders and/or more than once than those illustrated.

For ease of understanding, the exemplary workflow of FIGS. 3A and 3B is described below with reference to implementation on various components of the exemplary embodiment of FIG. 1. However, those having ordinary skill in the art will appreciate that such description with reference to FIG. 1 is not intended to be limiting, and the workflow of FIGS. 3A and 3B can be implemented on a variety of teleoperated surgical systems, including a teleoperated surgical system having a patient side cart configuration like that of FIG. 12, for example. Further, the exemplary workflows are described in terms of electrical energy being the type of flux delivered to the surgical instrument, but as above, those skilled in the art will understand that other flux types can be delivered and are contemplated as within the scope of the present disclosure.

With reference now to the FIGS. 3A and 3B, as well as the system components in the exemplary embodiment of FIG. 1, in various exemplary embodiments, at 302 in FIG. 3A, a determination is made that one or more surgical instruments 1001 are installed at the patient side cart 1000. This determination can be made in various ways, including but not limited to for example, providing one or more memory structure reader devices (shown schematically at 1003 in FIG. 1) at the patient side cart 1000, for example, in proximity to or associated with each actuation interface assembly 1004. The instrument reader devices can read corresponding memory storage structures provided on the surgical instruments and containing various information about the surgical instruments, such as for example, instrument type, number of uses, etc., as those skilled in the art are familiar with.

Exemplary instrument reader devices can include, but are not limited to, for example, RFID sensors that read a unique RFID tag that is disposed on each surgical instrument; a memory chip (e.g., a SRAM or EEPROM memory chip) reader that can interface with and receive data from a unique memory chip provided on each surgical instrument; a barcode reader; and/or a magnetic medium reader (e.g., magnetic strip reader). Those having ordinary skill in the art will appreciate other types of reader devices can be used that have the ability to read stored information from a readable or readable and writable memory storage structure associated with the instrument. Such memory storage structure reader devices can be proximity-based in that their ability to read the unique information with which an instrument memory storage device is programmed relies on the instrument being in close range, e.g., coupled or engaged, with a respective actuation interface assembly 1004 of the patient side cart.

In addition to detecting instrument presence, a workflow in accordance with an exemplary embodiment can determine the instrument type of an instrument installed at an actuation interface assembly 1004 of a patient side cart. For example, the instrument reader devices associated with each actuation interface assembly 1004, e.g., RFID and/or memory chip readers, can determine instrument type and other information regarding an instrument based on the programmed information on the unique memory storage structure (e.g., RFID tag and/or memory chip). With regard to instrument type, the unique identifier information associated with a respective surgical instrument can include whether or not it is a surgical instrument configured for energy delivery (e.g., an electrosurgical instrument) and what type of energy it is configured to deliver (e.g., bipolar, monopolar, mixed mode, etc.).

Other types of proximity-based sensing devices also may be used, in lieu of or in addition to, for example, the RFID and/or memory chip readers, to detect that a surgical instrument 1001 is in an installed position at an actuation interface assembly 1004. For example, and as described in more detail below, a proximity-based sensing device can be disposed in the interface actuation assemblies 1004 and configured to sense when a transmission housing 1003 of a surgical instrument 1001 is engaged therewith so as to confirm a surgical instrument is in an accurate and installed position at a respective actuation interface assembly. In this way, it is possible to confirm instrument installation at the patient side cart 1000.

At step 304, the information obtained by the instrument reader and/or instrument installation sensing devices can be sent as signal information to the controller 3004, as those of ordinary skill in the art would have familiarity with, and the controller 3004 can thus determine the instrument types that are installed at the respective actuation interface assemblies at the patient side cart.

At 306, in at least one exemplary embodiment, the controller 3004 can output feedback regarding at least the instrument type, and optionally the confirmed installation, of each respective instrument 1001 that is installed at each respective actuation interface assembly 1004. By way of example, such information may be provided on display 3006 and/or display 2006 to enable a surgeon at the surgeon side console 2000 to know which input devices (e.g., 2010, 2020)

will operate which instruments 1001 upon an input command being provided at one of those input devices, with the surgeon also being provided with information regarding which input devices are mapped to control which instrument arms.

At 308, if a plurality of electrosurgical instruments are determined to be installed at the patient side cart 1000, a determination can be made at the controller 3004 which of the electrosurgical instruments is in an energy connection state by detecting the electrosurgical instruments that have an electrical energy transmission cable engaged therewith. Various exemplary embodiments are described in more detail below with reference to FIGS. 4-11 of non-limiting exemplary embodiments of "cable presence" sensing devices that can be used to provide a signal to the controller 3004 indicating that a respective electrosurgical instrument has an energy transmission cable in engagement therewith. Based on the signals indicative of whether and which electrosurgical instrument(s) are in an energy connection state, the controller can control the energy delivery to the various installed electrosurgical instruments.

At 312 the controller 3004 can control the energy generator (e.g., 3002 or others not shown in FIG. 1) to which an electrosurgical instrument 1001 is in electrical communication (e.g., send a signal closing a relay at the energy generator 3002) to deliver energy upon receipt of an energy input command from the surgeon side console 2000. In various exemplary embodiments, it is contemplated that an electrosurgical instrument can be configured to deliver differing types of energy, such as, for example, bipolar and monopolar, respectively. In such case it is contemplated that in at least one exemplary embodiment differing energy generators may be provided, with the energy transmission cable connecting the instrument to one of the generators depending on the energy type desired for the surgical procedure being performed. Again, the controller 3004 can send a signal to the energy generator requested based on an energy input command at the surgeon side console 2000. In various exemplary embodiments, one of the pedals 2010 can be associated with providing bipolar energy while another is associated with providing monopolar energy, and respective energy generators can be utilized to supply one of those types of energies. Other configurations also are contemplated and the input devices at the surgeon side console can be mapped with one or more energy generators in numerous ways within the controller, and such mapping information shared with the surgeon, without departing from the scope of the present disclosure. By way of nonlimiting example, a left bank of pedals can be mapped to control energy delivery to instruments that are being operated by the left hand gripping mechanism 2020 of the surgeon side console, while a right bank of pedals can be mapped to control energy delivery to instruments that are being operated by the right hand gripping mechanism 2020. For this and other positional mapping that can be utilized, reference is made to U.S. patent application Ser. No. 14/028,006, filed Sep. 16, 2013 (for "METHODS AND SYSTEMS FOR ASSIGNING INPUT DEVICES TO ROBOTIC SURGICAL INSTRUMENT FUNCTIONS"), which claims priority to U.S. Provisional Application No. 61/702,166, filed Sep. 17, 2012, both of which are incorporated by reference herein in their entireties. Each bank could also have differing energy types associated with it; for example one pedal of each bank could be mapped to supply energy from a monopolar energy source and another pedal of each bank could be mapped to supply energy from a bipolar energy source. Those having ordinary skill in the art would understand how to make appropriate modifications based on the present disclosure to accommodate various formats for mapping energy input devices at the surgeon side console with energy delivery at the patient side cart.

At step 310, if it is determined that there is not more than one electrosurgical instrument 1001 that is in an energy connection state, then the controller 3004 at 314 may output feedback indicating which instrument 1001 is in the energy connection state. This can permit the surgeon to know that if a given energy input command is provided at the surgeon side console, for example, via depression of a pedal 2010 that is configured to provide an energy input command to the controller 3004, which of the installed instruments that are electrosurgical instruments will be electrically activated, for example, to perform a cautery procedure on the patient.

If at 310 the controller 3004 determines that more than one of the installed electrosurgical instruments 1001 (only one being depicted in FIG. 1) is in an energy connection state, then the controller 3004 in an exemplary embodiment can implement a control scheme to prohibit energy delivery from one or more energy generators in cases where a potential ambiguity exists as to which of the instruments in a connection state would be electrically activated.

For example, with reference now to FIG. 3B, the controller 3004 at 316 can determine, based on the instrument type information determined at 304, whether or not more than one of the instruments determined to be in the connection state are the same energy type. For example, if it is determined that two or more electrosurgical instruments that are in an energy connection state are the same energy type (e.g., two bipolar instruments or two monopolar instruments), then, as shown at 318 of the flow diagram of FIG. 3B, the controller 3004 in an exemplary embodiment prohibits the delivery of energy from any energy generators of the system due to the ambiguity of which instrument will be electrically activated upon an energy input command (which may be, e.g., an input for a particular energy type mapped to an input device such as, for example, a pedal 2010 at the surgeon side console 2000) associated with more than one of the electrosurgical instruments that are in the energy connection state. By way of example, if at 316 a determination is made that two or more surgical instruments 1001 that are in an energy connection state are bipolar energy type instruments, then, even upon receiving an energy input command from the surgeon side console, the controller 3004 will not transmit the requisite signal to the energy generator(s) in the system to deliver energy.

In an exemplary embodiment, in the case where one or more of the surgical instruments 1001 that are in an energy connection state is a mixed mode instrument, the controller 3004 can determine to which energy generator (e.g., bipolar or monopolar) the instrument is in communication with based on detecting which of differing energy transmission cable types (e.g., bipolar or monopolar) is in engagement with the instrument. For example, as will be better understood from the description of the exemplary embodiments of FIGS. 4-11, a mixed mode surgical instrument may include two differing connection receptacles for bipolar energy supply and monopolar energy supply, respectively. Energy transmission cable sensing devices associated with the differing energy transmission cables may be used to detect when the differing cables are engaged with the surgical instrument. The energy type of the mixed mode instrument can then be effectively determined by detecting which energy transmission cable is engaged therewith. Based on this detection, if it is determined at 316 that the mixed mode surgical instrument is effectively of the same energy type as another instrument, including another mixed mode instrument of the same effective energy type, then even upon receiving an energy input command from the surgeon side console, the controller 3004 at 318 will not transmit the requisite signal to the energy generator(s) in the system to deliver energy.

At 320 in FIG. 3B, the controller 3004 also can output fault detection feedback indicating that two or more electrosurgical instruments of the same energy type are detected to be in an energy connection state, leading to an ambiguous energy connection condition. For example, such feedback may be provided at the display 3006 and/or the display 2006 and may include audible and/or visual feedback in various exemplary embodiments. In an exemplary embodiment, one or more of displays 2006, 3006 can provide visual feedback indicating which instruments are in a connection state and/or indicating that the system is in a configuration wherein energy will not be delivered to the surgical instruments.

Figure 13A:
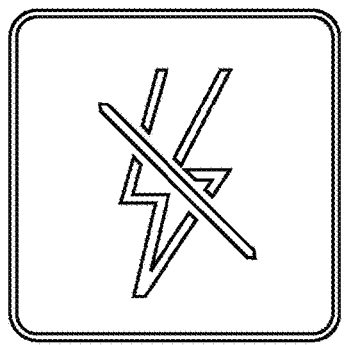
FIGS. 13A-13C show exemplary embodiments of visual feedback indicators in accordance with the present disclosure.
Figure 13B:
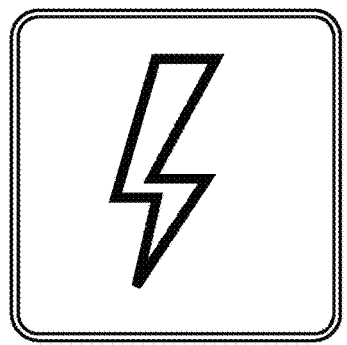
Figure 13C:
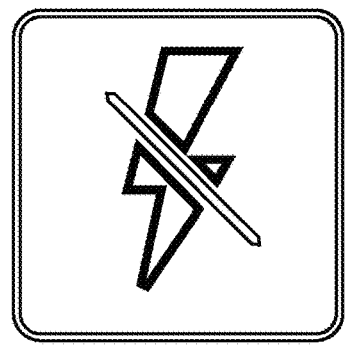

By way of non-limiting example only, FIGS. 13A-13C show exemplary icons that can be provided as visual feedback to indicate various states of an instrument for which an energy input command has been input at the surgeon side console. The icons in FIGS. 13A-13C can be displayed to show that an energy transmission cable is not connected (FIG. 13A), the surgical system is in a ready to activate energy state for a given surgical instrument (FIG. 13B), or the surgical system is in an ambiguous energy state (FIG. 13C) and thus energy activation will not be permitted. In an exemplary embodiment, the icons can be displayed on a display, such as display 2006 and/or 3006 for example, and can be displayed in proximity to the name of the instrument they correspond to which also can be presented on the display. Those having ordinary skill in the art would appreciate numerous types of feedback, including other icons and/or other indications, could be presented to provide similar information to a user.

In various exemplary embodiments, the surgical system continuously monitors state changes, including, for example, monitoring of the energy connection states and types of the installed surgical instruments. Thus, upon a change in the energy connection state or otherwise rectifying any ambiguous condition determination, the control method and system returns to the previous workflow step to continue with the workflow, as described in further detail below.

If, on the other hand, at 316 the controller 3004 determines that more than one electrosurgical instrument of the same type is not in an energy connection state, then at 322 in FIG. 3B the controller 3004 can in accordance with an exemplary embodiment implement a control scheme whereby it confirms that the electrosurgical instrument of a particular energy type is in a current master-slave relationship with the surgeon side console, in other words "in following," as explained further below. For example, in some exemplary embodiments of teleoperated surgical systems encompassed within the scope of the present disclosure, there are fewer master input devices (e.g., two gripping mechanisms 2020 at the surgeon side console 2000) that are operable at a given time than there are actuation interface assemblies with installed surgical instruments (e.g., 3 or more at the patient side cart 1000). In such a situation, the surgeon side console 2000 is used to identify to the controller 3004 which of the plurality of actuation interface assemblies will be mapped and under control of a given master input devices. In the example above, the surgeon side console 2000 identifies to the controller which of two actuation assemblies 1004 is mapped in a current master-slave relationship with the two gripping mechanisms 2020. When an actuation interface assembly is in a master-slave relationship, the actuation interface assembly, and consequently the surgical instrument installed at that actuation interface assembly, are designated as "in following" and a signal indicative of that status is provided to the controller 3004.

In the workflow of FIG. 3B, therefore, in various exemplary embodiments, as depicted at 322, the controller 3004 upon receipt of an energy input command signal from the surgeon side console 2000 confirms that the surgical instrument 1001 that the energy input command will activate is "in following," as described above. If at 322 the designated instrument that would be activated by the energy input command is determined not to be "in following," at 324 the controller 3004 prohibits energy from being delivered by the energy generator associated with that energy input command. For example, the controller 3004 will not send a signal closing a relay or otherwise providing input to the energy generator to supply energy to the instrument. Prohibiting energy delivery in this situation can enhance safety in the event that an instrument that is not "in following" is removed from the patient or at a position that the surgeon is not aware of due to the lack of a master-slave control over the instrument.

The controller 3004 also can output fault detection feedback signal at 326 indicating that the instrument for which an energy input command was requested at the surgeon side console 2000 is not "in following." For example, such feedback may be provided at the display 3006 or the display 2006 and may include audible and/or visual feedback in various exemplary embodiments.

If instead at 322, the controller 3004 confirms that the surgical instrument 1001 that will be energy activated based on the energy input command at the surgeon side console 2000 that is received as an energy input command signal at the controller 3004 is "in following," then at 328 the controller 3004 will permit energy from an energy generator to be delivered to that instrument. For example, the controller 3004 will send a signal to the energy generator associated with the energy input command to close a relay and supply energy to the instrument. It should be noted that if two differing energy type instruments (e.g., bipolar and monopolar) are installed, in an energy connection state, and confirmed to be in following, then upon receipt of an energy input command for the particular energy type of those instruments from the surgeon side console, the controller 3004 can permit energy generator(s) to supply energy to both of those electrosurgical instruments.

Figure 4A:
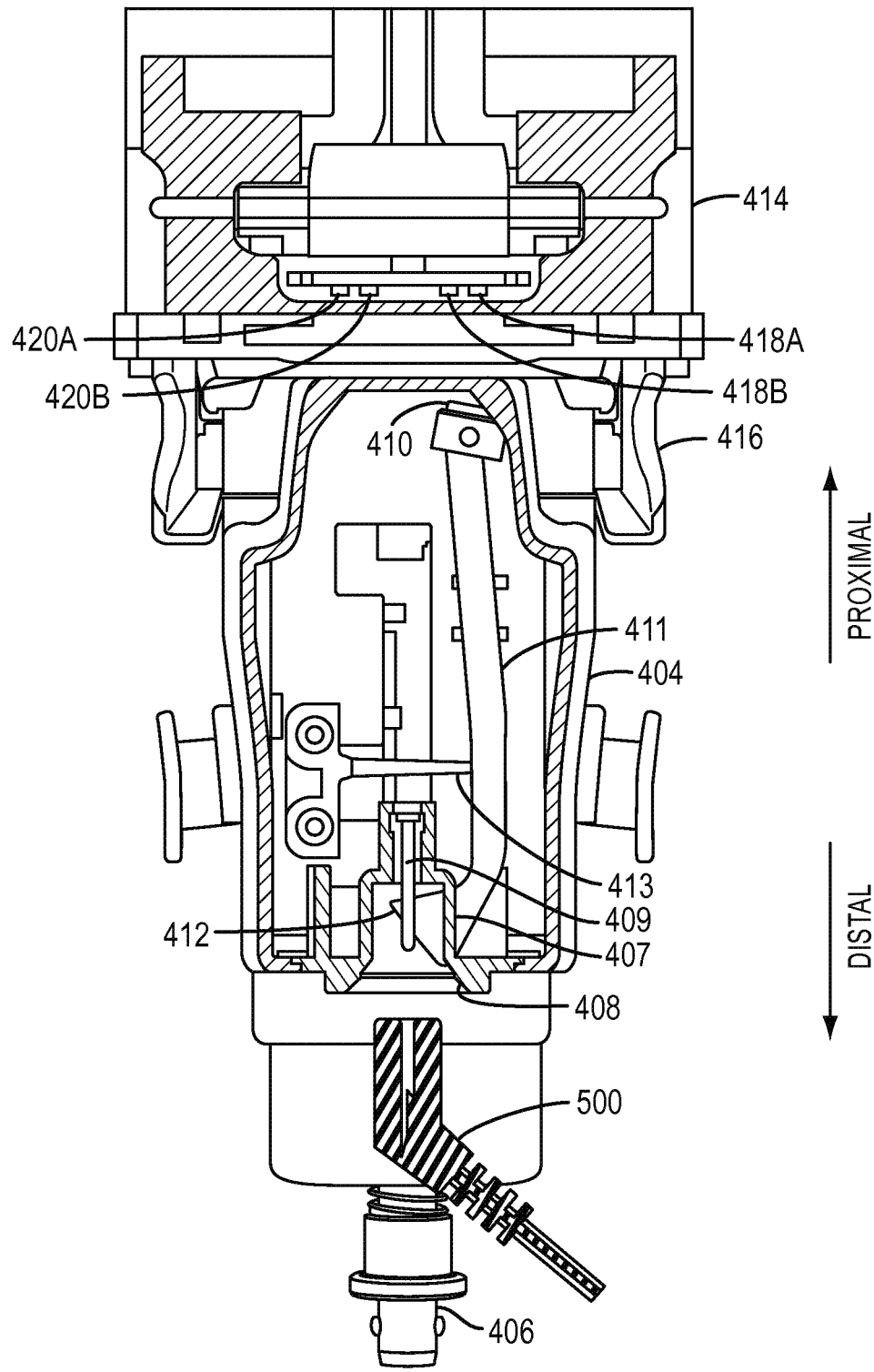
FIGS. 4A and 4B are partial cut-away views illustrating an exemplary embodiment of an electrosurgical instrument housing in an installed position at patient side cart, respectively illustrating the electrosurgical instrument not in an energy connection state and in an energy connection state in accordance with the present disclosure.
Figure 4B:
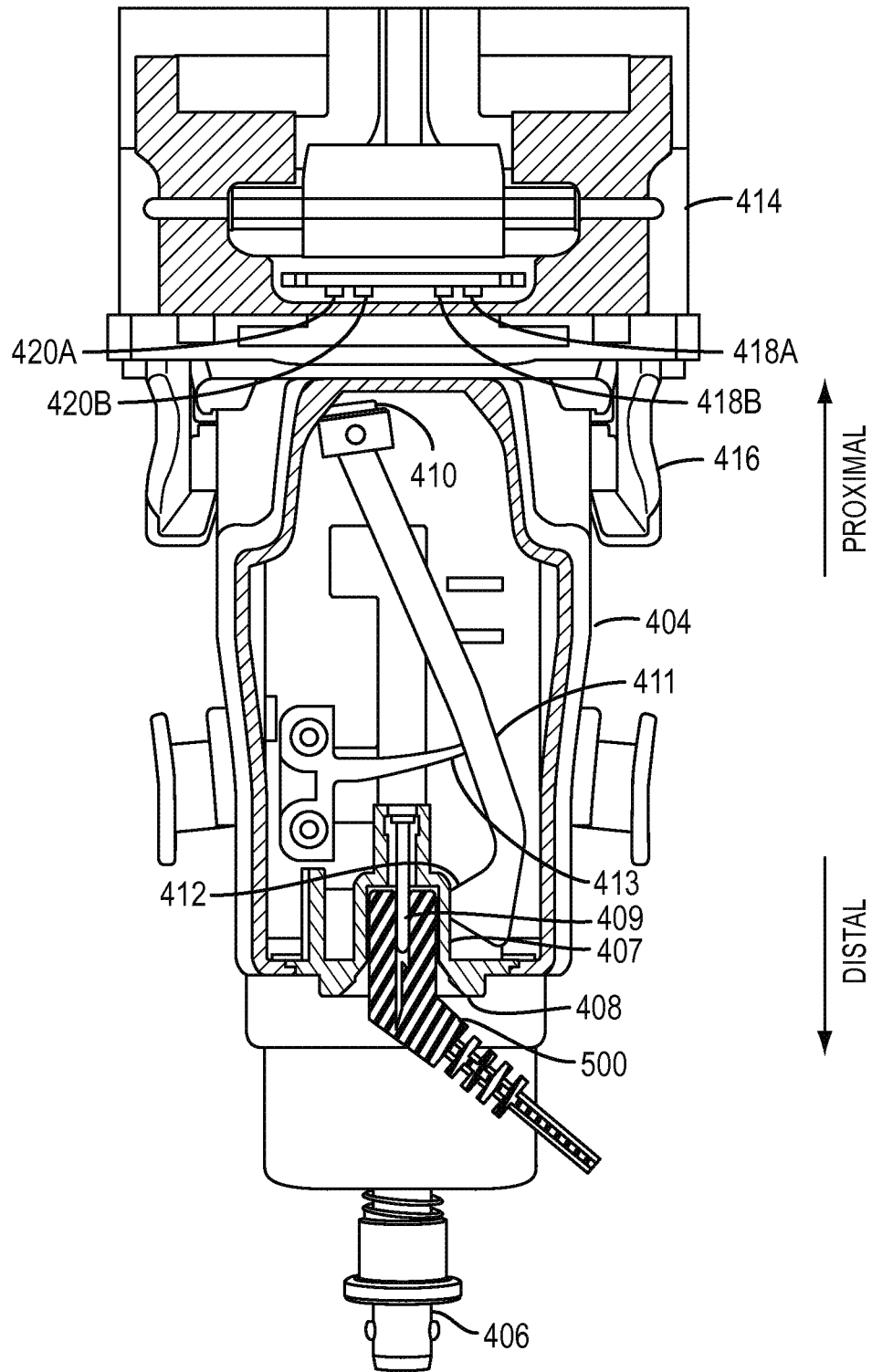

Referring now to FIGS. 4A and 4B, which depict cutaway views of a portion of an electrosurgical instrument housing in an installed position relative to an actuation interface assembly, one exemplary embodiment of a system for detecting both an installed position and energy connection state of the instrument is depicted. In the exemplary embodiment of FIGS. 4A and 4B, an electrosurgical instrument housing 404 is depicted in an installed position at an actuation interface assembly 414. The shaft and distal end portion of the surgical instrument that would connect to the housing at 406 is not depicted in FIGS. 4A and 4B. A connector receptacle 407 is disposed toward a distal end of the housing 404 and leads to an opening 408 that is accessible at an external surface of the housing 404. The opening 408 and connector receptacle 407 are sized to receive in mating engagement an energy transmission cable 500 (shown in partial view in FIGS. 4A and 4B), as those having ordinary skill in the art would be readily familiar. In a mating engaged state within the connector receptacle 407, the energy transmission cable 500 also is placed into contact with an energy contact member 409 to provide a closed energy circuit and permit energy (e.g., electrical current) to be transmitted from the cable 500 to the contact 409 which ultimately is in energy communication with the distal end effector of the surgical instrument that delivers the energy to the patient. Although in FIGS. 4A and 4B, the cable 400 is depicted as having the female connection portion and the contact 409 is the male portion, those having ordinary skill in the art would appreciate that the male and female energy contact connector portions could be reversed.

In the exemplary embodiment of FIGS. 4A and 4B, the actuation interface assembly 414 is provided with a proximity-based sensing device that can be utilized to detect that the surgical instrument housing 404 is in an installed position. More specifically, one or more Hall sensors (e.g., one or more of Hall sensors 418A, 418B, 420A, and 420B as described in further detail below) is mounted in the actuation assembly interface 414. In turn, a magnet 410 can be disposed in the housing 404 at a location such that upon a correct engagement of the housing 404 with the sterile adapter 416 of the actuation interface assembly 414 that places the instrument housing 404 in an installed position relative to the interface actuation assembly 414 and thus patient side cart, the magnet 410 is placed in sensing proximity to the one or more Hall sensors 418A, 418B, 420A, 420B. Detection of the magnetic field of the magnet 410 by the one or more Hall sensors 418A, 418B, 420A, 420B causes the Hall sensors to send a signal to the controller 3004 indicating the surgical instrument associated with the housing 404 is in an installed position with the actuation interface assembly 414 at the patient side cart. As will be better understood from the following description, it is desirable to provide a proximity-based sensing device and corresponding sensed component on the instrument (or vice versa) that enable detection of the instrument in the installed position regardless of other changes in instrument state, including the energy connection state, that may occur. Further, it may be desirable to provide a sensing device that is configured and arranged to be brought into sensing proximity with a sensed component upon accurate installation of the instrument at a manipulator arm, in order to be able to confirm such accuracy in installation of the instrument.

As described above with reference to the workflow of FIGS. 3A and 3B, the instrument, e.g., the instrument housing 404, also can be provided with a memory storage device (not shown), such as, for example, a RFID tag, EPROM, Flash EPROM, EEPROM, SRAM, etc., for storing instrument information and that is readable at the patient side cart 1000 when the housing 404 is installed at the actuation interface assembly 414.

In the exemplary embodiment of FIGS. 4A and 4B, the magnet 410 is disposed on the proximal end of a moveable arm 411 (e.g., a flexure arm), with the proximal and distal directions again being labeled in FIGS. 4A and 4B. More specifically, the arm 411 is mounted via a flexible hinge 413 within the housing 404. A cam feature 412 is provided at an end portion of the arm 411 opposite to the end at which the magnet 410 is mounted. In a configuration wherein the electrosurgical instrument is not in an energy connection state, as shown in FIG. 4A, with the cable 500 not received in mating engagement in the connector receptacle 407, the cam feature 412 projects through a slotted opening in the wall of the receptacle 407 and into the interior of the receptacle 407. In this state, the flexure arm 411 is in a first position (e.g., with the flexible hinge 413 in an unflexed configuration). In the position of the arm 411 in FIG. 4A, the magnet 410 is in sensing proximity to the one or more Hall sensors 418A, 418B.

In an energy connection state of the electrosurgical instrument, as illustrated in FIG. 4B, the mating engagement of the energy transmission cable 500 in the connector receptacle 407 places the energy transmission cable 500 into engagement with the cam feature 412. This engagement causes the cam feature 412 to move to the position shown in the FIG. 4B, which in turn causes the flexible hinge 413 to flex to pivot the arm 411 about the hinge 413 and move the magnet 410 to the position shown in FIG. 4B. In the position shown in FIG. 4B, the magnet 410 is in sensing proximity to one or more Hall sensors 420A, 420B in the actuation interface assembly 414.

Upon sensing the magnet 410, the one or more Hall sensors 420A, 420B can send a signal to the controller 3004 indicating that the electrosurgical instrument associated with the housing 404 is in an energy connection state.

Although it is contemplated as within the scope of the present disclosure to use one Hall sensor 418 and one Hall sensor 420, providing Hall sensor pairs 418A, 418B and 420A, 420B can provide an ambiguous state detection feature that permits the controller 3004 to determine that the energy transmission cable is only partially received in the receptacle 407 but not entirely received therein (e.g., as shown in FIG. 4B) while also determining that the instrument is in an installed position. In this situation, in an exemplary embodiment, the controller can prohibit energy delivery to the instrument.

Figure 5C:
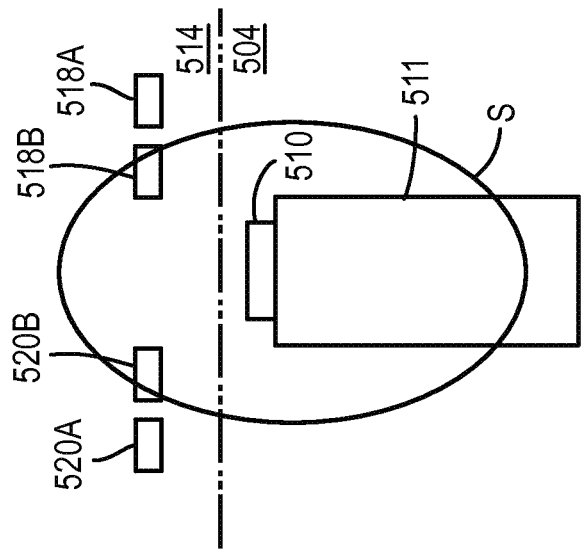
FIGS. 5A-5C are schematic views depicting three differing states of an exemplary embodiment of a magnet and Hall sensor system utilized for detecting a surgical instrument installation and energy connection state in accordance with the present disclosure.
Figure 5B:
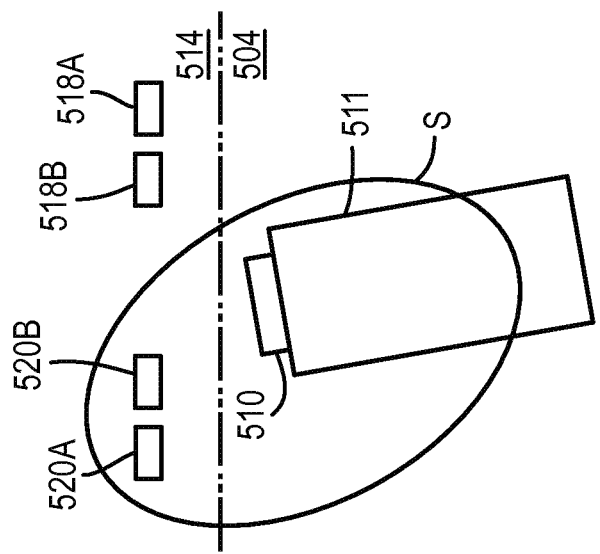
Figure 5A:
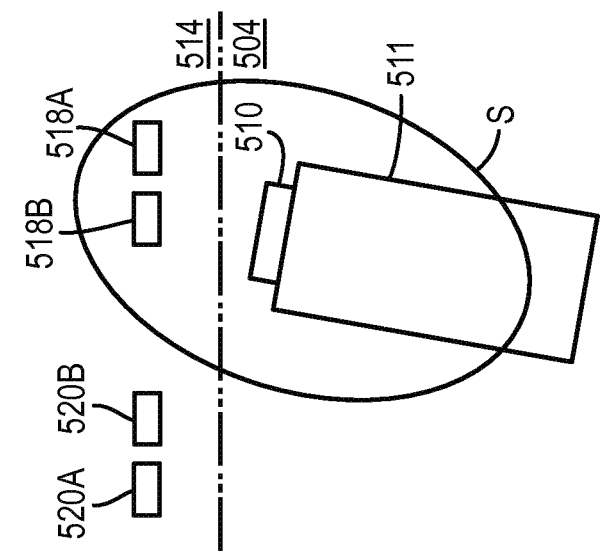

Referring now to FIGS. 5A-5C, an exemplary embodiment schematically depicting the use of two sets of Hall sensors in the actuation interface assembly to detect a magnet in the electrosurgical instrument housing is illustrated. In FIGS. 5A-5C, the dashed line depicts the interface between the electrosurgical instrument housing 504 and the actuation interface assembly 514. Similar to the description of FIGS. 4A and 4B, FIGS. 5A-5C depict a magnet 510 disposed on the proximal end of a moveable arm 511 and two sets of Hall sensors 518A, 518B and 520A, 520B disposed in the actuation interface assembly 514. As shown in FIG. 5A, the arm 511 and magnet 510 are in a first position when the electrosurgical instrument is in an installed position at the actuation interface assembly 514 and with the electrosurgical instrument not in an energy connection state (i.e., the energy transmission cable is not received in the connector receptacle as in the embodiment of FIG. 4A). In the first position, the magnet 511 is in sensing proximity to both of the Hall sensors 518A, 518B as shown by the region S which indicates the magnetic flux range of the magnet 510 having a strength sufficient to be detected by the Hall sensors 518A, 518B. In the first position, again as depicted by the region S, the Hall sensors 520A, 520B are not in sensing proximity to the magnet 510 and therefore the magnet 510 is not sensed by those Hall sensors.

In FIG. 5B, the arm 511 and magnet 510 are in a second position as a result of the electrosurgical instrument being placed in an energy connection state (i.e., the energy transmission cable is received in the connector receptacle as in the embodiment of FIG. 4B). In this position, the magnet 511 is in sensing proximity to both of the Hall sensors 520A, 520B as shown by the region S which indicates the magnetic flux range of the magnet 510 having a strength sufficient to be detected by the Hall sensors 520A, 520B. In the second position, again as depicted by the region S, the Hall sensors 518A, 518B are not in sensing proximity to the magnet 510 and therefore the magnet 510 is not sensed by those Hall sensors.

Turning now to FIG. 5C, the schematic illustration depicts an installed position of the electrosurgical instrument housing 504 relative to the actuation interface assembly 514, however the energy connection state is ambiguous as a result of the energy transmission cable being received in the connector receptacle to a degree sufficient to move the arm 511 but not completely engaged such that the arm 511 moves to the second position of FIG. 5B. In this configuration wherein the arm 511 is either in a state of travel between or otherwise placed in a position between the first and second positions shown in FIGS. 5A and 5B, respectively, the magnet 510 is in sensing proximity of one Hall sensor of each of the Hall sensor pairs. That is, as shown by the region S, when the magnet 510 is located between the first and second positions, it is in sensing proximity to Hall sensor 518B and 520B. In this position and based on the Hall sensor 518B and 520B sensing the magnet 510 and sending signals to the controller 3004, the controller can determine that the electrosurgical instrument is in an installed position but that the energy connection state is ambiguous. In this case, the controller can control the system to prohibit energy delivery from an energy generator to the electrosurgical instrument, and optionally also provide a fault detection feedback signal, for example, to provide visual and/or audible feedback indicating that the energy connection state is ambiguous and/or the cable connection should be verified.

Providing the Hall sensor and magnet configuration of the exemplary embodiment of FIGS. 5A-5C can ensure that if the instrument is in an installed position, the magnet is always detected regardless of the energy connection state of the electrosurgical instrument and regardless of the position of the magnet throughout its travel between the first position and the second position. In this manner, there is a reduced risk of mistakenly determining that the electrosurgical instrument is not installed when it actually is and is in a state of potential energy connection (e.g., the energy transmission cable is plugged in sufficiently for electrical contact to be made in the instrument housing). Such an incorrect determination could lead to an ambiguity if an energy input command is provided at the surgeon side console, thereby resulting in potential inadvertent energy activation at the electrosurgical instrument.

As those of ordinary skill in the art will appreciate, a variety of mechanisms may be utilized to provide signals to a controller of a teleoperated surgical system to determine that an instrument is in an installed position at an actuation interface assembly of a manipulator arm and/or the energy connection state of an installed electrosurgical instrument. For example, those having ordinary skill in the art will appreciate that the exemplary embodiments shown and described with respect to FIGS. 4 and 5 can be modified to incorporate various types of sensing technologies that can be implemented to alter a state in reaction to the energy connection state of the electrosurgical instrument (e.g., in response to the energy transmission cable being in a connected or unconnected state), including but not limited to, for example, optical, magnetic, electrical (e.g., switches), etc.

FIGS. 6-11 depict some exemplary, nonlimiting alternative embodiments that are contemplated by the present disclosure. With reference to FIGS. 6A and 6B, a schematic view of a set of Hall sensors 618 and 620 associated with the actuation interface assembly 614 and a magnet 610 on an arm 611 in the electrosurgical instrument housing 604 that moves up and down in response to an energy transmission cable 600 being placed in engagement with the housing is depicted. FIG. 6A shows the electrosurgical instrument not in an energy connection state (e.g., energy transmission cable 600 not received in the connector receptacle 607) and FIG. 6B shows the electrosurgical instrument in an energy connection state (e.g., energy transmission cable 600 received in the connector receptacle 607 and in electrical connection with electrical contact 609). In FIG. 6A, the magnet 610 on the proximal end of the arm 611 is in sensing proximity S to the Hall sensor 618, which can provide a signal to a controller at the control cart that the electrosurgical instrument is in an installed position. In FIG. 6B, the connector cable 600 acts on the arm 611 to move the arm 611 and the magnet 610 upward, thereby positioning the magnet 610 in sensing proximity, designated by S, of both Hall sensors 618 and 620. This provides another signal to the controller of the system that the electrosurgical instrument is in an energy connection state. A spring return 630 can be used to ensure the arm 611 returns to the position of FIG. 6A upon removal of the cable 600.

In another exemplary embodiment, as opposed to moving into the range of a second one or pair of Hall sensors, movement of the arm in response to the engagement of the energy transmission cable could cause the arm to act on a mechanical switch, for example through a sterile adaptor of an actuation interface assembly, to close a circuit in the actuation interface assembly. FIGS. 7A and 7B show a schematic depiction of an exemplary embodiment showing such a configuration using an arm 711 of an electrosurgical instrument housing 704, similar to that of the embodiment of FIGS. 4A and 4B. Such a mechanical switch embodiment can be configured for use with the embodiments of FIGS. 4 and 6, for example, and a magnet 710 on the arm 711 can be sensed by one or more Hall sensors 718, associated with an actuation interface assembly 714, in the first position (e.g., not in energy connection state; FIG. 7A) to provide the signal to the controller indicating the instrument is installed. Then, upon movement of the arm to the second position (e.g., energy connection state; FIG. 7B) as a result of the connection of the energy transmission cable, the arm 711 can engage a cam feature 724 to mechanically close a switch on a circuit 722 to send the signal to the controller indicating the energy connection state. In an alternative embodiment, the switch feature of FIGS. 7A and 7B may be provided through an optical sensing mechanism, for example, a portion of the cam feature could move into and out of an interrupting position of a light path, which in turn could send a signal to the controller or otherwise close circuit. Those having ordinary skill in the art would understand how to modify the sensor configuration to implement such an optical sensing scheme.

Figure 6A:
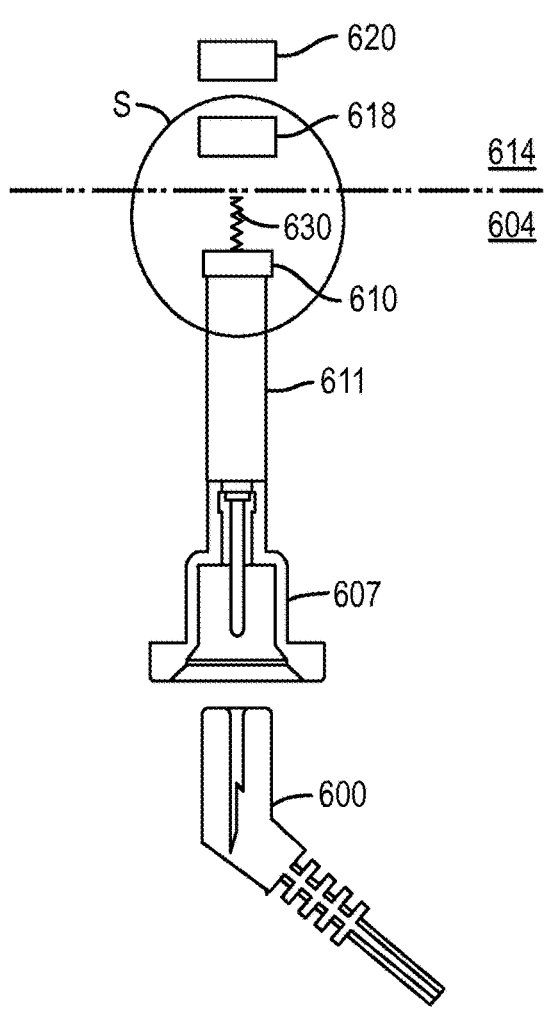
FIGS. 6A and 6B depict schematic side cross-sectional views of an actuation interface assembly and an electrosurgical instrument, respectively illustrating the electrosurgical instrument not in an energy connection state and in an energy connection state, in accordance with the present disclosure.
Figure 6B:
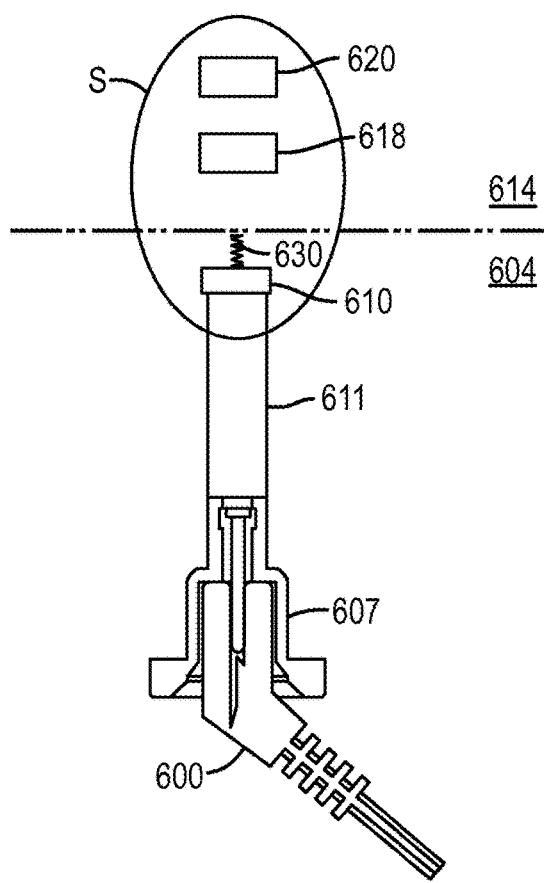
Figure 7A:
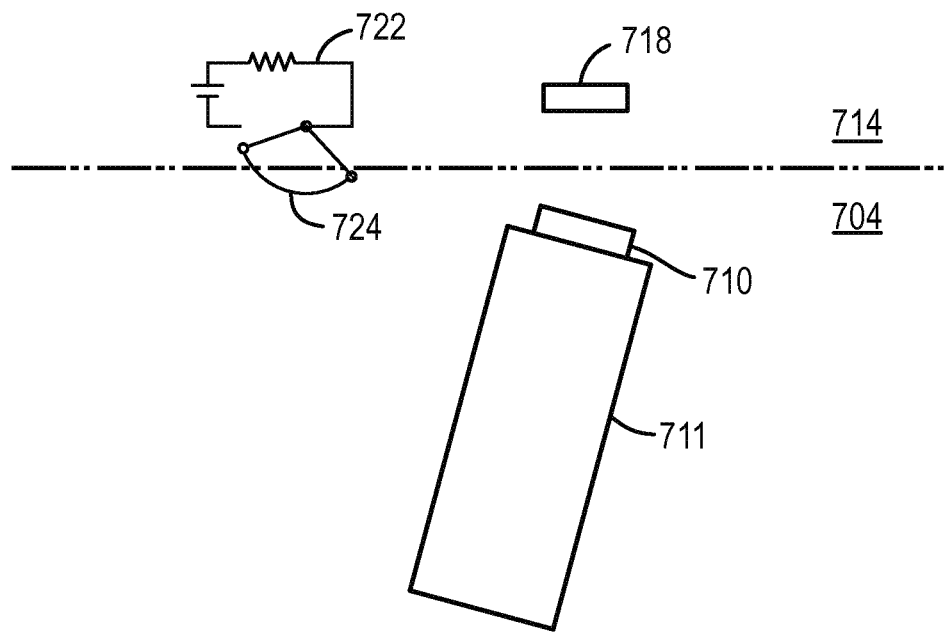
FIGS. 7A and 7B depict schematic side views of a moveable arm of an electrosurgical instrument housing and an actuation interface assembly, respectively illustrating the arm not in an energy connection state and in an energy connection state, in accordance with the present disclosure.
Figure 7B:
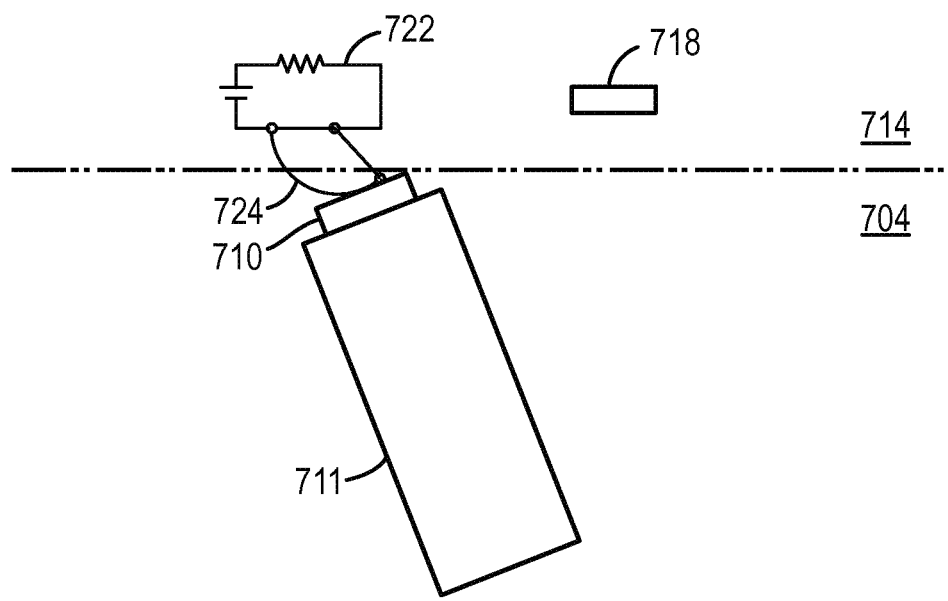
Figure 8A:
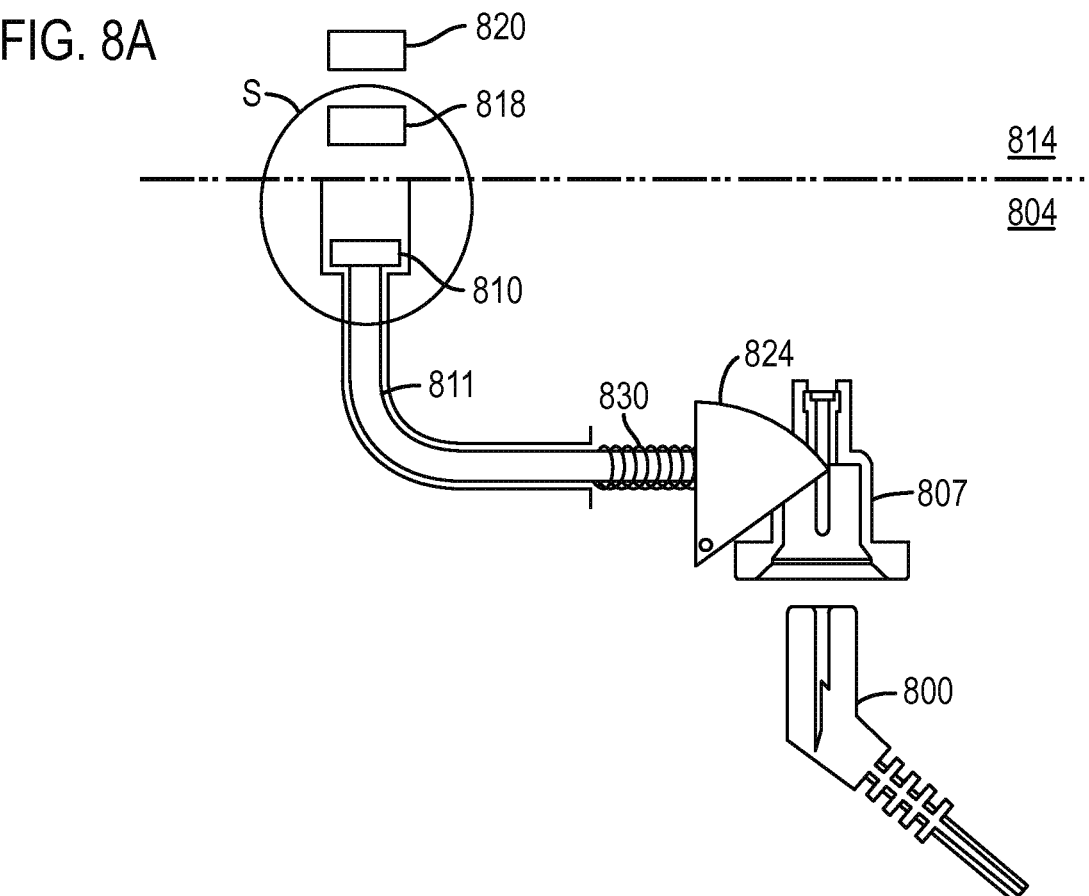
FIGS. 8A and 8B depict schematic side cross-sectional views of a moveable arm of an electrosurgical instrument housing and an actuation interface assembly, respectively illustrating the arm not in an energy connection state and in an energy connection state, in accordance with the present disclosure.
Figure 8B:
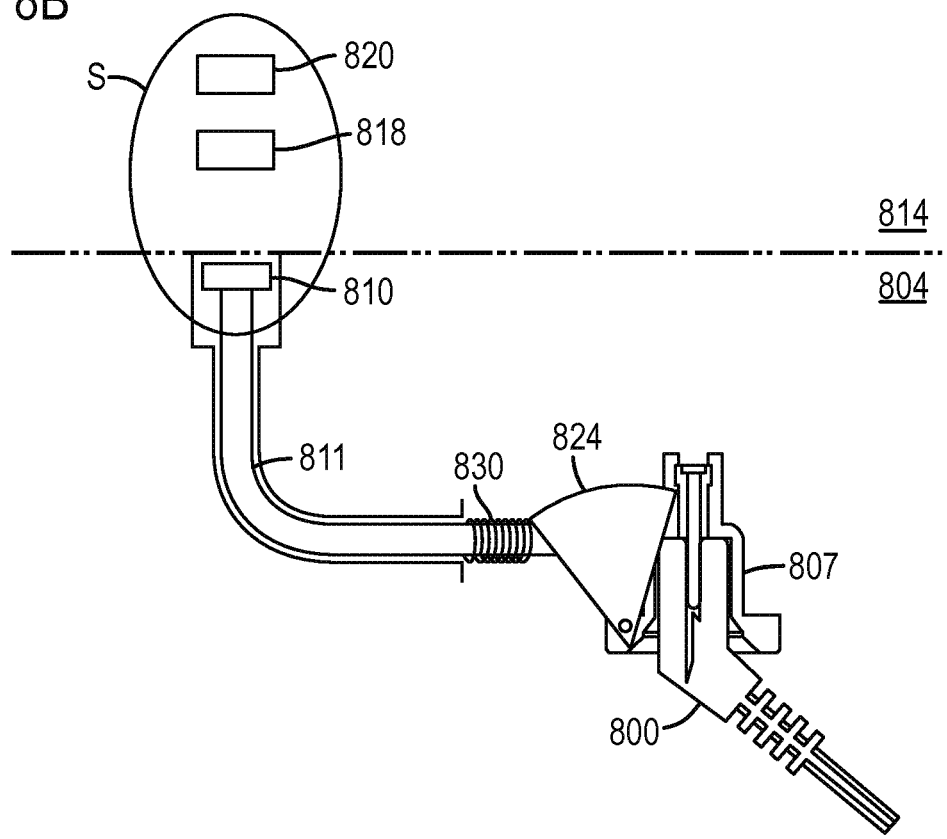

FIGS. 8A and 8B schematically depict an embodiment similar to FIGS. 6A and 6B except that an arm 811 carrying a magnet 810 on its proximal end is in connection with a spring-biased (e.g., via spring 830) rotary cam 824 that interacts with the energy transmission cable 800 to move the arm 811 and magnet 810 disposed on the proximal end of the arm 811 up and down in the electrosurgical instrument housing 804 and from sensing proximity of only one Hall sensor 818, associated with an actuation interface assembly 814, (see region S in FIG. 8A) to sensing proximity of two Hall sensors 818 and 820 (see region S in FIG. 8B). Thus, when the energy transmission cable 800 is not received in the receptacle housing 807, the magnet 810 is in the position shown in FIG. 8A and the surgical instrument is determined to not be in an energy connection state. When the energy transmission cable 800 is received in the receptacle housing 807, the magnet is moved to the position shown in FIG. 8B and the surgical instrument is determined to be in an energy connection state.

Figure 9A:
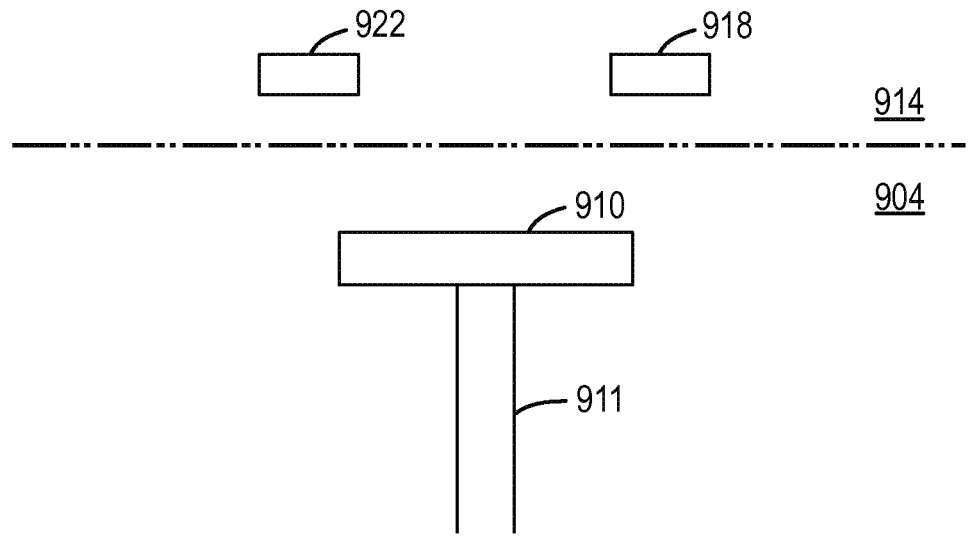
FIGS. 9A and 9B depict schematic side cross-sectional views of an actuation interface assembly and a magnetizable member of an electrosurgical instrument housing, respectively illustrating the magnetizable member in a first, non-magnetized position and in a second, magnetized position, in accordance with the present disclosure.
Figure 9B:
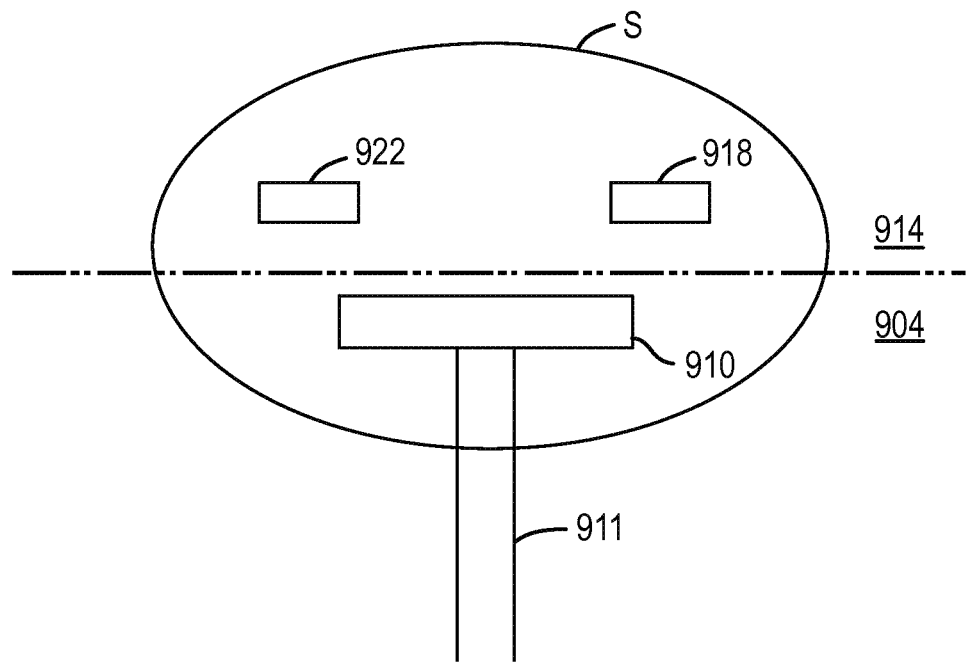
Figure 10:
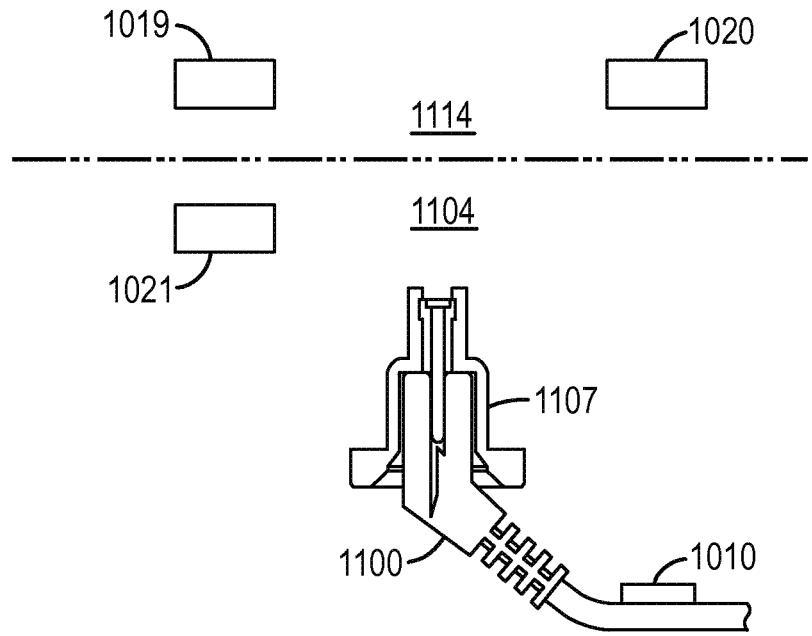
FIG. 10 depicts a schematic side cross-sectional view of an energy transmission cable of an electrosurgical instrument including RFID sensors and an actuation interface assembly including RFID readers to detect the RFID sensor when the electrosurgical instrument is in an installed position, in accordance with the present disclosure.

In various exemplary embodiments, a permanent magnet and Hall sensor could be used in combination as the sensing mechanism in the actuation interface assembly, and a steel or otherwise magnetizable member could be used in the electrosurgical instrument housing. With reference to the exemplary embodiment depicted schematically in FIGS. 9A and 9B, a magnetizable member 910 is provided within the electrosurgical housing 904. The magnetizable member 910 can be provided on an arm 911 that is movable from the position shown in FIG. 9A to the position shown in FIG. 9B, for example, in response to the energy transmission cable (not shown) being disengaged or engaged with the housing 904, as has been described above with respect to other exemplary embodiments. In the position of FIG. 9A, the member 910 is not in proximity to a permanent magnet 922 and Hall sensor 918, associated with an actuation interface assembly 914, such that the member 910 is nonmagnetized and is accordingly not sensed by the Hall sensor 918. In FIG. 9B, showing an energy connection state of the surgical instrument, the position of the member 910 is such that it is within the range of the permanent magnet 922 and the Hall sensor 918 such that the permanent magnet 922 causes the member 910 to become magnetized. The magnetic flux range of the member 910 in the position of FIG. 9B is in sensing proximity, as indicated by the region S, to the Hall sensor 918, which thereby can provide a signal to the controller to indicate the electrosurgical instrument 904 is in an energy connection state.

In yet another exemplary embodiment, it is contemplated that a readable and writable memory device, such as, for example, an RFID tag and/or a memory chip, provided on the electrosurgical instrument could be configurable so as to change information upon engagement of the energy transmission cable to the electrosurgical instrument. For example, the readable and writable memory device (e.g., RFID tag and/or memory chip) could be configurable such that in addition to providing instrument information, including the type (e.g., energy type) of the instrument, the information stored could be changed from indicating a no energy connection state to an energy connection state depending on whether or not the energy transmission cable is in mating electrical connection with the housing.

In various alternative exemplary embodiments, the present disclosure contemplates sensing the cable presence by providing one or more sensible mechanisms on the cable itself. For example, with reference to FIG. 10, it may be possible to, in addition to a RFID tag 1021 associated with the electrosurgical instrument (e.g., disposed at housing 1104), an additional RFID tag 1010 can be placed on the energy transmission cable 1100. More than one RFID reader (e.g., two readers 1019 and 1020 shown in FIG. 10) could be provided at the actuation interface assembly 1114 and both the electrosurgical instrument and RFID tags 1021 and 1010 may be readable only by a respective one of the RFID readers, for example, based on proximity to the same. For example, in the exemplary embodiment of FIG. 10, RFID reader 1019 can sense RFID tag 1021 when the electrosurgical instrument is in an installed position relative to the actuation interface assembly 1114, and RFID reader 1020 could sense RFID tag 1010 when the energy transmission cable 1200 is in mating engagement with the electrosurgical instrument connector receptacle 1107 in the housing 1104. Placement of the RFID tag and reader associated with reading the energy transmission cable could be selected so that the RFID tag on the cable comes into sensing proximity to the reader when the cable is placed in mating electrical connection with the electrosurgical instrument.

Figure 11:
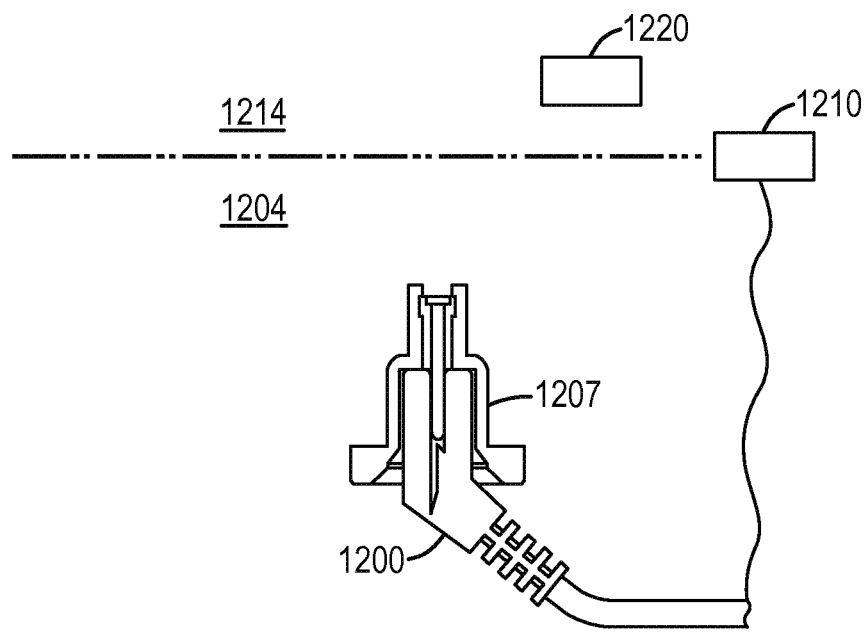
FIG. 11 depicts a schematic side cross-sectional view of an energy transmission cable of an electrosurgical instrument including a sensible mechanism and an actuation interface assembly including a sensor to detect the sensible mechanism when the electrosurgical instrument is in an installed position, in accordance with the present disclosure.

In accordance with an alternative exemplary embodiment, with reference to FIG. 11, a magnet 1210 or other sensible mechanism may be provided on the energy transmission cable 1200. The magnet 1210 or other sensible mechanism may be attached to the cable 1200 by a leash and positionable by a user such that when the cable is placed in mating connection with the connector receptacle 1207 of the electrosurgical instrument housing 1204, the magnet 1210 or other sensible mechanism is able to be positioned relative to the actuation interface assembly so as to be placed in sensing proximity with a sensor 1220, associated with an actuation interface assembly 1214, which may be for example a Hall sensor 1220. To facilitate accurate placement, the sensor 1220 may be positioned external to the actuation interface assembly and/or if placed internally, some designation could be provided on the actuation interface assembly observable by a user so as to facilitate placement of the sensible mechanism.

In yet another exemplary embodiment, the energy transmission cable may be directly sensed at the patient side cart by, for example, interrupting a light path or other optical sensing mechanism that changes state from a disconnected configuration of the cable to a mating electrical connection configuration of the cable with the electrosurgical instrument. As another example, when the transmission cable makes electrical contact with the electrosurgical instrument, a light circuit could be closed to light up an LED or other light that is in turn sensed by a sensor in the actuation interface assembly or otherwise at the patient side cart.

Exemplary embodiments, including the various operational methods described herein, can be implemented using computing hardware (computing apparatus) and/or software, such as, in a non-limiting example, any computer that can store, retrieve, process and/or output data and/or communicate with other computers. The results produced can be displayed on a display of the computing hardware. One or more programs/software comprising algorithms to affect the various responses and signal processing in accordance with various exemplary embodiments of the present disclosure can be implemented by a processor of or in conjunction with the electronics/control cart 3000 (for example as part of the controller 3004 thereof), and may be recorded on computer-readable media including computer-readable recording and/or storage media. Examples of the computer-readable recording media include a magnetic recording apparatus, an optical disk, a magneto-optical disk, and/or a semiconductor memory (for example, RAM, ROM, etc.). Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW. Those of ordinary skill in the art of teleoperated surgical systems are generally familiar with the controller and processing capabilities, including various hardware and software components, utilized in the operation of those systems and would understand based on the present disclosure how to modify the same to perform the various methods and control schemes described herein.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present disclosure. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims. In particular, based on the present disclosure, those of ordinary skill in the art would understand a variety of differing sensing mechanisms and arrangements that could be employed to detect the presence of various types of flux transmission conduits in a connection state with a surgical instrument, and the particular sensing mechanisms and arrangements set forth in the illustrated embodiments and described above should not be construed as limiting. For example, the depicted energy transmission cables could have differing connection features, or hoses with luer fittings or other connection features to connect to the surgical instrument can be used, with those of ordinary skill in the art appreciating that various modifications to the interaction between such flux transmission conduits with the surgical instrument housing to carry out the teachings and principles of the present disclosure.

Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

What is claimed is:

1. A method comprising:
   receiving at a controller of a teleoperated surgical system:
   at least one signal indicating which of a plurality of surgical instruments installed at a patient side cart of the teleoperated surgical system are in an energy connection state, and
   information of an energy type of each surgical instrument installed at the patient side cart and in the energy connection state; and
   controlling energy transmission from one or more energy supply sources to the surgical instruments installed at the patient side cart based on which of the plurality of surgical instruments are in the energy connection state;
   wherein receiving the at least one signal indicating which of the plurality of surgical instruments are in the energy connection state comprises receiving a plurality of signals indicating that more than one of the plurality of surgical instruments are in the energy connection state; and
   wherein the controlling the energy transmission comprises prohibiting or permitting energy transmission based on the information of the energy type of each of the plurality of surgical instruments in the energy connection state.

2. The method of claim 1, further comprising:
   receiving information at the controller that an energy type of the plurality of surgical instruments in the energy connection state differ from each other;
   wherein controlling the energy transmission comprises permitting the energy transmission to each of the plurality of surgical instruments in the energy connection state based on an energy input command received at the controller.

3. The method of claim 1, wherein:
   receiving the at least one signal indicating which of the plurality of surgical instruments are in the energy connection state comprises receiving a signal indicating that only one of the plurality of surgical instruments is in the energy connection state; and
   the controlling the energy transmission comprises permitting energy transmission to the surgical instrument in the energy connection state based on an energy input command received at the controller.

4. The method of claim 1, wherein receiving the at least one signal indicating which of the plurality of surgical instruments is in the energy connection state comprises receiving a signal from a sensor at the patient side cart.

5. The method of claim 4, wherein receiving the signal from the patient side cart comprises receiving a signal from a sensor at a patient side cart that detects a presence of an energy transmission cable in engagement with a respective surgical instrument in an energy connection state.

6. The method of claim 4, wherein the receiving the signal from the patient side cart comprises receiving a signal from a Hall sensor detecting a proximity of a magnet associated with a respective surgical instrument in an energy connection state.

7. The method of claim 1, further comprising outputting a command via the controller to provide feedback indicating which of the plurality of surgical instruments is in the energy connection state.

8. The method of claim 1, further comprising receiving, at the controller, information from at least one memory storage structure of each of the plurality of surgical instruments.

9. The method of claim 8, wherein receiving, at the controller, information from at least one memory storage structure comprises receiving, at the controller, information regarding an electrosurgical energy type each of the plurality of surgical instruments in the energy connection state is configured to deliver.

10. The method of claim 9, wherein the information regarding the electrosurgical energy type comprises an indication that each of the plurality of surgical instruments in the energy connection state is configured to deliver one or more of bipolar electrosurgical energy, monopolar electrosurgical energy, and mixed mode electrosurgical energy.

11. The method of claim 9, wherein receiving, at the controller, information from at least one memory storage structure of each of the plurality of surgical instruments comprises receiving, at the controller, information from at least one of a memory chip, a radio frequency identification tag, a barcode, and a magnetic strip.

* * * * *